US008845559B2

(12) United States Patent
Darlington et al.

(10) Patent No.: US 8,845,559 B2
(45) Date of Patent: Sep. 30, 2014

(54) METHOD AND APPARATUS FOR TREATING TISSUES WITH HIFU

(75) Inventors: Gregory P. Darlington, Snohomish, WA (US); Michael J. Connolly, Bothell, WA (US); Justin A. Reed, Seattle, WA (US); Jessica E. Parsons, Kirkland, WA (US); Roland Horth, Newburyport, MA (US); John Murkowski, Seattle, WA (US)

(73) Assignee: Mirabilis Medica Inc., Bothell, WA (US)

( * ) Notice: Subject to any disclaimer, the term of this patent is extended or adjusted under 35 U.S.C. 154(b) by 438 days.

(21) Appl. No.: 12/573,840

(22) Filed: Oct. 5, 2009

(65) Prior Publication Data

US 2010/0210976 A1 Aug. 19, 2010

Related U.S. Application Data

(60) Provisional application No. 61/102,804, filed on Oct. 3, 2008.

(51) Int. Cl.
| | |
|---|---|
| *A61H 1/00* | (2006.01) |
| *A61H 1/02* | (2006.01) |
| *A61H 5/00* | (2006.01) |
| *A61N 7/02* | (2006.01) |
| *A61N 7/00* | (2006.01) |
| *A61B 19/00* | (2006.01) |

(52) U.S. Cl.
CPC ........... *A61N 7/02* (2013.01); *A61N 2007/0082* (2013.01); *A61B 2019/5276* (2013.01)
USPC .................... 601/3; 601/2; 600/437; 600/439

(58) Field of Classification Search
USPC ...................... 600/437, 439; 601/2–4; 606/27
See application file for complete search history.

(56) References Cited

U.S. PATENT DOCUMENTS

| | | | |
|---|---|---|---|
| 3,470,868 | A | 10/1969 | Krause |
| 3,480,002 | A | 11/1969 | Flaherty |
| 3,676,584 | A | 7/1972 | Plakas |
| 3,941,112 | A | 3/1976 | Habert |
| 4,059,098 | A | 11/1977 | Murdock |

(Continued)

FOREIGN PATENT DOCUMENTS

| | | | |
|---|---|---|---|
| EP | 0301360 B1 | 2/1989 | |
| EP | 0614651 A1 | 9/1994 | |

(Continued)

OTHER PUBLICATIONS

International Search Report and Written Opinion mailed Dec. 27, 2011, issued in corresponding International Application No. PCT/US2011/031129, filed Apr. 4, 2011.

(Continued)

*Primary Examiner* — James Kish
(74) *Attorney, Agent, or Firm* — Christennsen O'Connor Johnson Kindness PLLC

(57) ABSTRACT

A method for treating a desired volume of tissue using HIFU or other energy modality to ablate a pattern of elemental treatment volumes each having a volume that is greater than that of the focal zone of the HIFU transducer but smaller than the overall volume of the desired treatment volume. In one embodiment, the pattern of elemental treatment volumes are arranged to form a shell which partially or wholly encapsulates the desired volume of tissue, which then necroses in situ due to effects other than direct HIFU damage (including some combination of ischemia, thermal conduction, inflammation, apoptosis, etc.). The necrosed tissue remains in the body and is subsequently resorbed and/or healed via normal body mechanisms.

31 Claims, 16 Drawing Sheets

(56) References Cited

U.S. PATENT DOCUMENTS

| | | |
|---|---|---|
| 4,097,835 A | 6/1978 | Green |
| 4,185,502 A | 1/1980 | Frank |
| 4,282,755 A | 8/1981 | Gardineer |
| 4,347,850 A | 9/1982 | Kelly-Fry |
| 4,484,569 A | 11/1984 | Driller |
| 4,665,913 A | 5/1987 | L'Esperance, Jr. |
| 4,742,829 A | 5/1988 | Law |
| 4,756,313 A | 7/1988 | Terwilliger |
| 4,835,689 A | 5/1989 | O'Donnell |
| 4,858,613 A | 8/1989 | Fry |
| 4,865,042 A | 9/1989 | Umemura |
| 4,893,624 A | 1/1990 | Lele |
| 4,938,217 A | 7/1990 | Lele |
| 5,005,579 A | 4/1991 | Wurster |
| 5,036,855 A | 8/1991 | Fry |
| 5,050,610 A | 9/1991 | Oaks |
| 5,080,101 A | 1/1992 | Dory |
| 5,080,102 A | 1/1992 | Dory |
| 5,080,660 A | 1/1992 | Buelna |
| 5,117,832 A | 6/1992 | Sanghvi |
| 5,234,429 A | 8/1993 | Goldhaber |
| 5,271,402 A | 12/1993 | Yeung |
| 5,391,140 A | 2/1995 | Schaetzle |
| 5,441,499 A | 8/1995 | Fritzsch |
| 5,471,988 A | 12/1995 | Fujio |
| 5,474,071 A | 12/1995 | Chapelon |
| 5,492,126 A | 2/1996 | Hennige |
| 5,520,188 A | 5/1996 | Hennige |
| 5,558,092 A | 9/1996 | Unger |
| 5,619,999 A | 4/1997 | Von Behren |
| 5,665,054 A | 9/1997 | Dory |
| 5,666,954 A | 9/1997 | Chapelon |
| 5,676,692 A | 10/1997 | Sanghvi |
| 5,720,287 A | 2/1998 | Chapelon |
| 5,762,066 A | 6/1998 | Law |
| 5,769,790 A | 6/1998 | Watkins |
| 5,810,007 A | 9/1998 | Holupka |
| 5,882,302 A | 3/1999 | Driscoll, Jr. |
| 5,976,092 A | 11/1999 | Chinn |
| 5,993,389 A | 11/1999 | Driscoll, Jr. |
| 6,002,251 A | 12/1999 | Sun |
| 6,007,499 A * | 12/1999 | Martin et al. ............... 601/3 |
| 6,042,556 A | 3/2000 | Beach |
| 6,050,943 A | 4/2000 | Slayton |
| 6,068,653 A | 5/2000 | LaFontaine |
| 6,071,239 A | 6/2000 | Cribbs |
| 6,083,159 A | 7/2000 | Driscoll, Jr. |
| 6,126,607 A | 10/2000 | Whitmore, III |
| 6,128,522 A * | 10/2000 | Acker et al. ............... 600/411 |
| 6,196,972 B1 | 3/2001 | Moehring |
| 6,217,530 B1 | 4/2001 | Martin |
| 6,254,601 B1 | 7/2001 | Burbank |
| 6,267,734 B1 | 7/2001 | Ishibashi |
| 6,315,741 B1 | 11/2001 | Martin |
| 6,390,973 B1 | 5/2002 | Ouchi |
| 6,425,867 B1 | 7/2002 | Vaezy |
| 6,432,067 B1 | 8/2002 | Martin |
| 6,451,013 B1 | 9/2002 | Bays |
| 6,461,314 B1 | 10/2002 | Pant |
| 6,488,639 B1 | 12/2002 | Ribault |
| 6,500,133 B2 | 12/2002 | Martin |
| 6,508,774 B1 | 1/2003 | Acker |
| 6,533,726 B1 | 3/2003 | Lizzi |
| 6,537,224 B2 | 3/2003 | Mauchamp |
| 6,602,251 B2 | 8/2003 | Burbank |
| 6,613,004 B1 | 9/2003 | Vitek |
| 6,618,620 B1 * | 9/2003 | Freundlich et al. ............. 607/27 |
| 6,626,855 B1 | 9/2003 | Weng |
| 6,633,658 B1 | 10/2003 | Dabney |
| 6,645,162 B2 | 11/2003 | Friedman |
| 6,666,835 B2 | 12/2003 | Martin |
| 6,676,601 B1 | 1/2004 | Lacoste |
| 6,692,450 B1 | 2/2004 | Coleman |
| 6,716,184 B2 | 4/2004 | Vaezy |
| 6,719,694 B2 | 4/2004 | Weng |
| 6,740,082 B2 | 5/2004 | Shadduck |
| 6,764,488 B1 | 7/2004 | Burbank |
| 6,840,936 B2 | 1/2005 | Sliwa, Jr. |
| 6,936,046 B2 | 8/2005 | Hissong |
| 7,063,666 B2 | 6/2006 | Weng |
| 7,090,643 B2 | 8/2006 | Fidel |
| 7,105,007 B2 | 9/2006 | Hibler |
| 7,175,596 B2 | 2/2007 | Vitek |
| 7,258,674 B2 | 8/2007 | Cribbs |
| 7,399,284 B2 | 7/2008 | Miwa |
| 7,452,357 B2 | 11/2008 | Voegele |
| 7,470,241 B2 | 12/2008 | Weng |
| 7,473,224 B2 | 1/2009 | Makin |
| 7,520,856 B2 | 4/2009 | Vaezy |
| 7,686,763 B2 | 3/2010 | Vaezy |
| 7,699,782 B2 | 4/2010 | Angelsen |
| 7,722,539 B2 | 5/2010 | Carter |
| 7,850,626 B2 | 12/2010 | Vaezy |
| 7,914,452 B2 | 3/2011 | Hartley |
| 7,993,289 B2 * | 8/2011 | Quistgaard et al. ............... 601/2 |
| 2001/0012934 A1 | 8/2001 | Chandrasekaran |
| 2002/0029036 A1 | 3/2002 | Goble |
| 2002/0065512 A1 | 5/2002 | Fjield |
| 2002/0120259 A1 | 8/2002 | Lettice |
| 2003/0004439 A1 | 1/2003 | Pant |
| 2003/0028111 A1 | 2/2003 | Vaezy |
| 2003/0060736 A1 | 3/2003 | Martin |
| 2003/0149380 A1 | 8/2003 | Fujimoto |
| 2003/0233045 A1 | 12/2003 | Vaezy |
| 2004/0030268 A1 | 2/2004 | Weng |
| 2004/0030269 A1 | 2/2004 | Horn |
| 2004/0039312 A1 * | 2/2004 | Hillstead et al. ............... 601/2 |
| 2004/0082859 A1 | 4/2004 | Schaer |
| 2004/0152986 A1 | 8/2004 | Fidel |
| 2004/0153126 A1 | 8/2004 | Okai |
| 2004/0242999 A1 | 12/2004 | Vitek |
| 2004/0243112 A1 | 12/2004 | Bendett |
| 2004/0243201 A1 | 12/2004 | Goldman |
| 2005/0038340 A1 | 2/2005 | Vaezy |
| 2005/0085726 A1 | 4/2005 | Lacoste |
| 2005/0101854 A1 | 5/2005 | Larson |
| 2005/0154431 A1 * | 7/2005 | Quistgaard et al. ............. 607/96 |
| 2005/0203399 A1 | 9/2005 | Vaezy |
| 2005/0256405 A1 | 11/2005 | Makin |
| 2005/0267454 A1 | 12/2005 | Hissong |
| 2006/0052701 A1 | 3/2006 | Carter |
| 2006/0122509 A1 | 6/2006 | Desilets |
| 2006/0264748 A1 | 11/2006 | Vaezy |
| 2007/0010805 A1 * | 1/2007 | Fedewa et al. ............... 606/27 |
| 2007/0016039 A1 | 1/2007 | Vortman |
| 2007/0066990 A1 | 3/2007 | Marsella |
| 2007/0194658 A1 | 8/2007 | Zhang |
| 2007/0197918 A1 | 8/2007 | Vitek |
| 2007/0238994 A1 | 10/2007 | Stecco |
| 2007/0255267 A1 | 11/2007 | Diederich |
| 2008/0033419 A1 | 2/2008 | Nields |
| 2008/0039724 A1 | 2/2008 | Seip |
| 2008/0051656 A1 | 2/2008 | Vaezy |
| 2008/0058683 A1 | 3/2008 | Gifford |
| 2008/0071165 A1 | 3/2008 | Makin |
| 2008/0086036 A1 | 4/2008 | Hartley |
| 2008/0114274 A1 | 5/2008 | Moonen |
| 2008/0125771 A1 | 5/2008 | Lau |
| 2008/0221647 A1 | 9/2008 | Chamberland |
| 2008/0281314 A1 | 11/2008 | Johnson |
| 2008/0312561 A1 * | 12/2008 | Chauhan ............... 601/2 |
| 2008/0319436 A1 | 12/2008 | Daniel |
| 2009/0036774 A1 | 2/2009 | Weng |
| 2009/0069677 A1 * | 3/2009 | Chen et al. ............... 600/439 |
| 2009/0228001 A1 | 9/2009 | Pacey |
| 2009/0281463 A1 | 11/2009 | Chapelon |
| 2009/0326420 A1 | 12/2009 | Moonen |
| 2010/0241005 A1 | 9/2010 | Darlington |
| 2011/0201929 A1 | 8/2011 | Vaezy |

FOREIGN PATENT DOCUMENTS

| | | |
|---|---|---|
| EP | 0734742 A2 | 10/1996 |
| EP | 1726267 A2 | 11/2006 |

(56) References Cited

FOREIGN PATENT DOCUMENTS

| | | |
|---|---|---|
| JP | 05023336 A | 2/1993 |
| JP | 2002536040 A | 10/2002 |
| JP | 2004534582 A | 11/2004 |
| JP | 2009-541000 A | 11/2009 |
| WO | 93/17646 A2 | 9/1993 |
| WO | 94/27502 A1 | 12/1994 |
| WO | 95/20360 A1 | 8/1995 |
| WO | 97/00646 A1 | 1/1997 |
| WO | 97/10768 A2 | 3/1997 |
| WO | 00/45706 A1 | 8/2000 |
| WO | 01/71380 A2 | 9/2001 |
| WO | 02/100486 A1 | 12/2002 |
| WO | 03/002189 A2 | 1/2003 |
| WO | 2004/073524 A1 | 9/2004 |
| WO | 2005/000097 A2 | 1/2005 |
| WO | 2006/097661 A1 | 9/2006 |
| WO | 2008/003910 A1 | 1/2008 |
| WO | 2010/040140 A2 | 4/2010 |

OTHER PUBLICATIONS

Daum, D.R., and Hynynen, K., "A 256-Element Ultrasonic Phased Array System for the Treatment of Large Volumes of Deep Seated Tissue," IEEE Transactions on Ultrasonics, Ferroelectrics, and Frequency Control 46 (5):1254-1268, Sep. 1999.

Enholm, J.K., et al., "Improved Volumetric MR-HIFU Ablation by Robust Binary Feedback Control," IEEE Transactions on Biomedical Engineering 57(1):103-113, Jan. 2010.

Mougenot, C., et al., "Automatic Spatial and Temporal Temperature Control for MR-Guided Focused Ultrasound Using Fast 3D MR Thermometry and Multispiral Trajectory of the Focal Point," Magnetic Resonance in Medicine 52:1005-1015, 2004.

Mougenot, C., et al., "Three-Dimensional Spatial and Temporal Temperature Control with MR Thermometry-Guided Focused Ultrasound (MRgHIFU)," Magnetic Resonance in Medicine 61:603-614, 2009.

Cain. C.A., and S.-I. Umemura, "Concentric-Ring and Sector-Vortex Phased-Array Applicators for Ultrasound Hyperthermia," IEEE Transactions on Microwave Theory and Techniques, 34(5):542-551, May 1986.

Ngo, F.C., et al., "An Experimental Analysis of a Sector-Vortex Phased Array Prototype," Ultrasonics Symposium, pp. 999-1002, 1989.

Umemura, S.-I., and C.A. Cain, "Acoustical Evaluation of a Prototype Sector-Vortex Phased-Array Applicator," IEEE Transactions on Ultrasonics, Ferroelectrics, and Frequency Control, 39(1)32-38, Jan. 1992.

International Search Report dated May 11, 2010, in International Application No. PCT/US2009/059589, filed Oct. 5, 2009.

International Search Report and Written Opinion mailed Oct. 26, 2010, issued in International Application No. PCT/US2010/026565, filed Mar. 8, 2010, 10 pages.

Chapelon, J.Y., et al., "The Feasibility of Tissue Ablation Using High Intensity Electronically Focused Ultrasound," Proceedings of the IEEE Ultrasonics Symposium, Baltimore, Oct. 31-Nov. 3, 1993, pp. 1211-1214.

Chen, L., et al., "Effect of Blood Perfusion on the Ablation of Liver Parenchyma With High-Intensity Focused Ultrasound," Physics in Medicine and Biology 38(11):1661-1673, Nov. 1993.

Cheng, S.-Q., et al., "High-Intensity Focused Ultrasound in the Treatment of Experimental Liver Tumour," Journal of Cancer Research and Clinical Oncology 123(4):219-223, Apr. 1997.

Coad, J.E., "Thermal Fixation: A Central Outcome of Hyperthermic Therapies," Proceedings of the SPIE Conference on Thermal Treatment of Tissue: Energy Delivery and Assessment III 5698: 15-22, San Jose, Calif., Jan. 23, 2005.

Delon-Martin, C., et al., "Venous Thrombosis Generation by Means of High-Intensity Focused Ultrasound," Ultrasound in Medicine & Biology 21(1):113-119, 1995.

Friedland, F., "Ultrasonic Therapy," American Journal of Nursing 59(9):1272-1275, Sep. 1959.

Fry, F.J., "Recent Bioeffects With Ultrasound on the Reproductive System and Solid Tumors," Journal of the Acoustical Society of America 63(Suppl. 1):S13, May 1978.

Hallberg, L., et al., "Menstrual Blood Loss—A Population Study: Variation at Different Ages and Attempts to Define Normality," Acta Obstetricia et Gynecologica Scandinavica 45(3):320-351, 1966.

Lee, J.M., et al., "Comparison of Wet Radiofrequency Ablation With Dry Radiofrequency Ablation and Radiofrequency Ablation Using Hypertonic Saline Preinjection: Ex Vivo Bovine Liver," Korean Journal of Radiology 5(4):258-265, Dec. 2004.

Lee, J.M., et al., "Wet Radio-Frequency Ablation Using Multiple Electrodes: Comparative Study of Bipolar Versus Monopolar Modes in the Bovine Liver," European Journal of Radiology 54:408-417, Jun. 2005.

Mittleman, R.S., et al., "Use of the Saline Infusion Electrode Catheter for Improved Energy Delivery and Increased Lesion Size in Radiofrequency Catheter Ablation," Pacing and Clinical Electrophysiology 18(5 Pt. 1):953-1081, May 1995.

Orsini-Meinhard, K, "UW Tech-Transfer Program Putting Discoveries to Work," The Seattle Times, May 27, 2007.

Rabkin, B.A., "Biological and Physical Mechanisms of HIFU-Induced Hyperecho in Ultrasound Images," Ultrasound in Medicine & Biology 32(11):1721-1729, Nov. 2006.

Rabkin, B.A., et al., "Hyperecho in Ultrasound Images of HIFU Therapy: Involvement of Cavitation," Ultrasound in Medicine and Biology 31(7):947-956, Jul. 2005.

Sanghvi, N. T., "High Intensity Focused Ultrasound (HIFU) for the Treatment of Rectal Tumors: A Feasibility Study," Proceedings of IEEE Ultrasonics Symposium 3:1895-1898, Cannes, France, Nov. 1-4, 1994.

"ThermoDox™ Animal Studies to Be Presented at 6th International Symposium on Therapeutic Ultrasound in Oxford, England," Aug. 30-Sep. 2, 2006, Celsion, Inc.,<http://www.celsion.com/news/releasedetail.dfm> [retrieved Oct. 8, 2007], 2 pages.

"ThermoDox™: Heat-Activated Liposome Drug," © 2007 Celsion, Inc., <http://www.celsion.com/products/ThermoDox.cfm> [retrieved Oct. 8, 2007], 3 pages.

Vaezy, S., et al., "Image-Guided Acoustic Therapy," Annual Review of Biomedical Engineering 3:375-390, Aug. 2001.

Winter, T.C., et al., "Focal Tumor Ablation: A New Era in Cancer Therapy," Ultrasound Quarterly 22(3):204-209, Sep. 2006.

Zanelli, C.I., et al., "Design and Characterization of a 10 cm Annular Array Transducer for High Intensity Focused Ultrasound (HIFU) Applications," Proceedings of the IEEE Ultrasonics Symposium 3:1887-1890, Cannes, France, Nov. 1-4, 1994.

Extended European Search Report mailed Feb. 26, 2010, issued in corresponding European Patent Application No. 07811847.8, filed Apr. 13, 2007, 7 pages.

International Search Report and Written Opinion mailed Jun. 26, 2009, issued in corresponding International Application No. PCT/US2008/082829, filed Jul. 11, 2008, 15 pages.

International Search Report and Written Opinion mailed May 18, 2010, issued in corresponding International Application No. PCT/US2009/053050, filed Aug. 6, 2009, 15 pages.

Notice of Reasons for Rejection mailed Mar. 12, 2012, issued in Japanese Patent Application No. 2009-505639, filed Apr. 13, 2007, 7 pages.

International Search Report and Written Opinion mailed Mar. 15, 2012, issued in International Application No. PCT/US2011/048331, filed Aug. 18, 2011, 8 pages.

Salomir, R., et al., "Local Hyperthermia With MR-Guided Focused Ultrasound: Spiral Trajectory of the Focal Point Optimized for Temperature Uniformity in the Target Region," Journal of Magnetic Resonance Imaging 12(4):571-583, Oct. 1, 2000.

European Search Report mailed Oct. 15, 2012, in European Application No. 09 81 8624, filed Oct. 5, 2009, 7 pages.

Japanese Office Action Notice of Reasons for Rejection dated Nov. 15, 2013, issued in Japanese Patent Application No. 2011-530293, filed Oct. 5, 2009, 5 pages.

\* cited by examiner

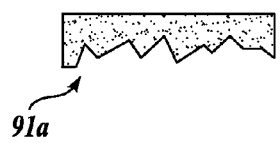
*Fig.3G.*
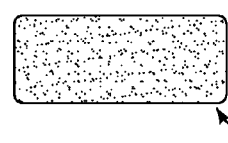
*Fig.3H.*
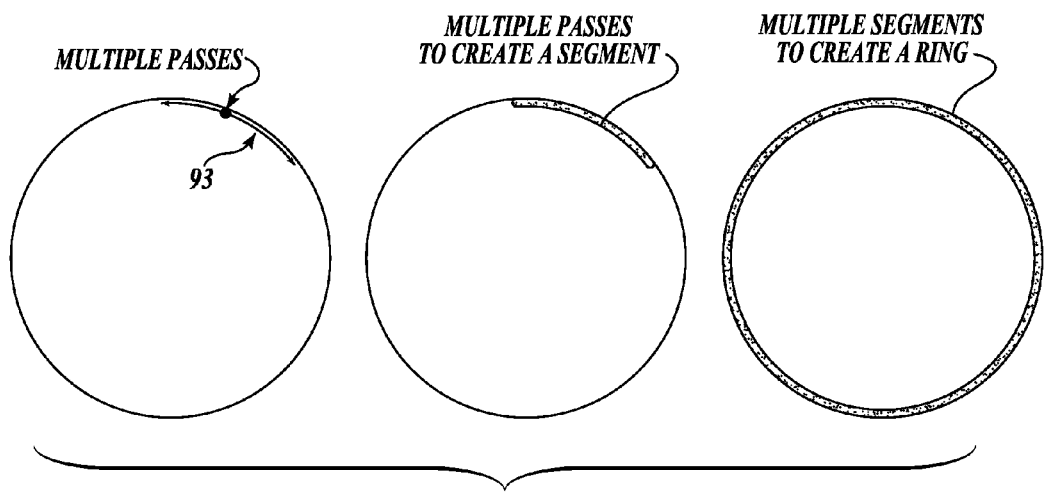
*Fig.3I.*

WOBBLE AXIS VARIES OVER THE RANGE OF 'α'
AND RADIUS AXIS VARIES OVER THE RANGE OF 'r'
TO CREATE UNIT VOLUME x AND y VARY TO CREATE A UNIT VOLUME

METHOD AND APPARATUS FOR TREATING TISSUES WITH HIFU

RELATED APPLICATION

This application claims the benefit under 35 U.S.C. Section 119(e) of U.S. Provisional Application 61/102,804 filed Oct. 3, 2008, which is herein incorporated by reference in its entirety.

FIELD OF THE INVENTION

The technology disclosed herein relates to methods and apparatus for the treatment of internal body tissues and in particular to the treatment of internal body tissues with high intensity focused ultrasound (HIFU).

BACKGROUND

There are numerous techniques that are currently used for the treatment of internal body tissues. For example, internal cancerous and non-cancerous tumors can be treated with a variety of techniques such as surgery, radiation and chemotherapy. Each of these techniques offers advantages and disadvantages. One promising non-invasive technology for treating internal body tissues is high intensity focused ultrasound (HIFU). With HIFU, high intensity ultrasound energy is focused at a desired treatment volume. The energy causes tissue destruction via both thermal and mechanical mechanisms.

One of the drawbacks of using HIFU to treat internal body tissues is the time required to treat a given volume of tissue. Currently proposed HIFU procedures may take up to 3 hours to treat a single tumor, which has contributed to poor acceptance of these procedures by both physicians and patients. In addition, the amount of energy required to completely ablate a large volume of tissue results in substantial thermal conduction outward from the ablation volume, which can raise the risk of thermal damage to surrounding healthy tissue.

Given these problems, there is a need for a method of treating internal body tissues in a manner that reduces treatment time, while improving both effectiveness and ease of use, and reducing total required energy deposition.

SUMMARY

To address the problems discussed above, the technology disclosed herein relates to a method of treating a desired volume of internal body tissues with energy from an energy source, which may include high intensity focused ultrasound (HIFU). Such energy sources could also include radiofrequency, radiation, microwave, cryotherapy, laser, etc. However the preferred embodiment is HIFU, due to its unique ability to be non-invasively focused deep inside body tissues without the need for punctures or incisions.

In one embodiment, a desired target volume of tissue is treated with HIFU by ablating a number of adjacent elemental treatment volumes to form "building blocks" used to treat the full target volume of tissue. Each elemental treatment volume is created by directing the focal zone of a HIFU transducer to ablate a sub-volume that is larger than the focal zone itself but smaller than the overall desired treatment volume. Each elemental treatment volume is created by repeatedly directing the focal zone of the HIFU transducer over the perimeter of the elemental treatment volume as treatment energy is being applied.

In one embodiment, a mechanical or electronic steering apparatus directs the focal zone of a HIFU beam around the perimeter of the elemental treatment volume until the tissue encompassed by the perimeter is ablated. In one embodiment, a center region of the elemental treatment volume is not directly ablated but is treated by thermal conduction as the perimeter is ablated.

In one embodiment, the disclosed technology includes a HIFU transducer that is configured to deliver treatment energy to a focal zone and a computer controlled beam steerer for repeatedly positioning the focal zone over a perimeter of an elemental treatment volume as treatment energy is applied.

In one embodiment, a pattern of elemental treatment volumes is created to form a shell of ablated tissue surrounding the treatment volume (similar to the geometry of an eggshell surrounding an egg). Treating a desired tissue volume using this type of shell ablation has two primary utilities in HIFU therapy: (1) In one embodiment, the ablated shell interrupts the supply of blood to the interior of the treatment volume, causing the otherwise untreated tissue located within the shell to ischemically necrose in situ. In this manner, the ischemic damage to the center of the volume results in the destruction of the entire volume over time, even though only the outer boundary is directly treated with HIFU. (2) In another embodiment, the elemental treatment volumes comprising the shell pattern are deposited in such a way that heat conduction toward the interior of the volume results in immediate thermal destruction of the inner tissue, even though only the outer boundary is directly ablated with HIFU energy. Both of these utilities provided by shell ablation serve to significantly improve the efficiency of HIFU therapy because they result in an effective tissue treatment volume that is larger than the volume directed ablated with HIFU energy. Leveraging either or both of these shell ablation advantages increases the throughput achieved by a given HIFU procedure.

In another embodiment, a number of elemental treatment volumes are created to fill or partially fill the target treatment volume. With this technique, a greater percentage of tissue within the treatment volume is directly necrosed by exposure to the ablating energy than is the case when only the outer boundary is ablated.

In another embodiment, a HIFU treatment device directs a focal zone of a HIFU transducer to move in a path to surround or envelop a tissue volume. The pattern in which the focal zone of the HIFU transducer is moved results in creating a series of ablated tissue toroids of varying diameter that are stacked to surround and envelop the tissue volume. In yet another embodiment, the focal zone is moved to create a spiral shell of ablated tissue to envelop the treatment volume.

In order to minimize treatment time and required user skill, one embodiment employs a computer-controlled mechanism to automatically move the HIFU focal zone and apply HIFU energy in such a manner to create the desired geometric shell while the user simply holds the applicator stationary.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this technology will become more readily appreci

FIG. 3G illustrates the uneven profile of treated tissue created by the application of energy in a single pass of the HIFU focus along the tissue volume;

FIG. 3H illustrates the more even profile of treated tissue created by the application of energy in multiple passes of the HIFU focus along the tissue volume;

FIG. 3I illustrates creating an arc or segment elemental treatment volume by directing a focal zone back and forth over a portion of the perimeter of the total treatment volume desired;

DETAILED DESCRIPTION

As indicated above, the technology disclosed herein relates to a method of treating internal body tissues such as uterine fibroids, benign or malignant tumors, or the like. Although the following description is directed to the use of the technology to treat uterine fibroids, it will be appreciated by those of skill in the art that the technology can be used to treat a volume of any internal body tissue. In one embodiment, the desired treatment volume is treated by creating a pattern of one or more elemental treatment volumes in the tissue. Though the technology disclosed herein describes several possible geometries for these elemental treatment volumes, each type of elemental volume shares the common feature that it is comprised of a volume of ablated tissue that is greater than the volume of the HIFU focal zone due to controlled motion of that focal zone around or along the elemental volume in a prescribed manner. The acoustic focal zone referenced herein is commonly defined as the volume encompassed by the −6 dB pressure contour of the acoustic waveform as measured from its spatial maximum. Those skilled in the art will recognize that the dimensions of this −6 dB pressure contour are also referred to as the full-width half-maximum, or FWHM, dimensions. A typical focal zone as implemented in the embodiments described herein is ovoid in shape, with FWHM dimensions of approximately 10 mm. in length along the beam axis and 2 mm. in width perpendicular to the beam axis.

In accordance with an embodiment of the disclosed technology, a desired volume of tissue to be treated is exposed to energy that ablates the tissue in a shell-like pattern, which completely or partially surrounds the tissue volume while only directly ablating the outer boundary. The tissue encompassed by the shell then remains in the body and necroses in situ due to effects other than direct ablation. These other effects causing in situ necrosis may include some combination of:

1. ischemic necrosis, resulting from partial or complete isolation of an encapsulated region from a surrounding blood supply;
2. indirect thermal necrosis, resulting from inward thermal conduction occurring during the creation of the ablated shell; and/or
3. secondary injury due to normal healing processes (inflammation, apoptosis, etc.).

The necrosed tissue located inside the ablated shell of the treated volume is subsequently resorbed and/or healed by normal body mechanisms.

Figure 1:
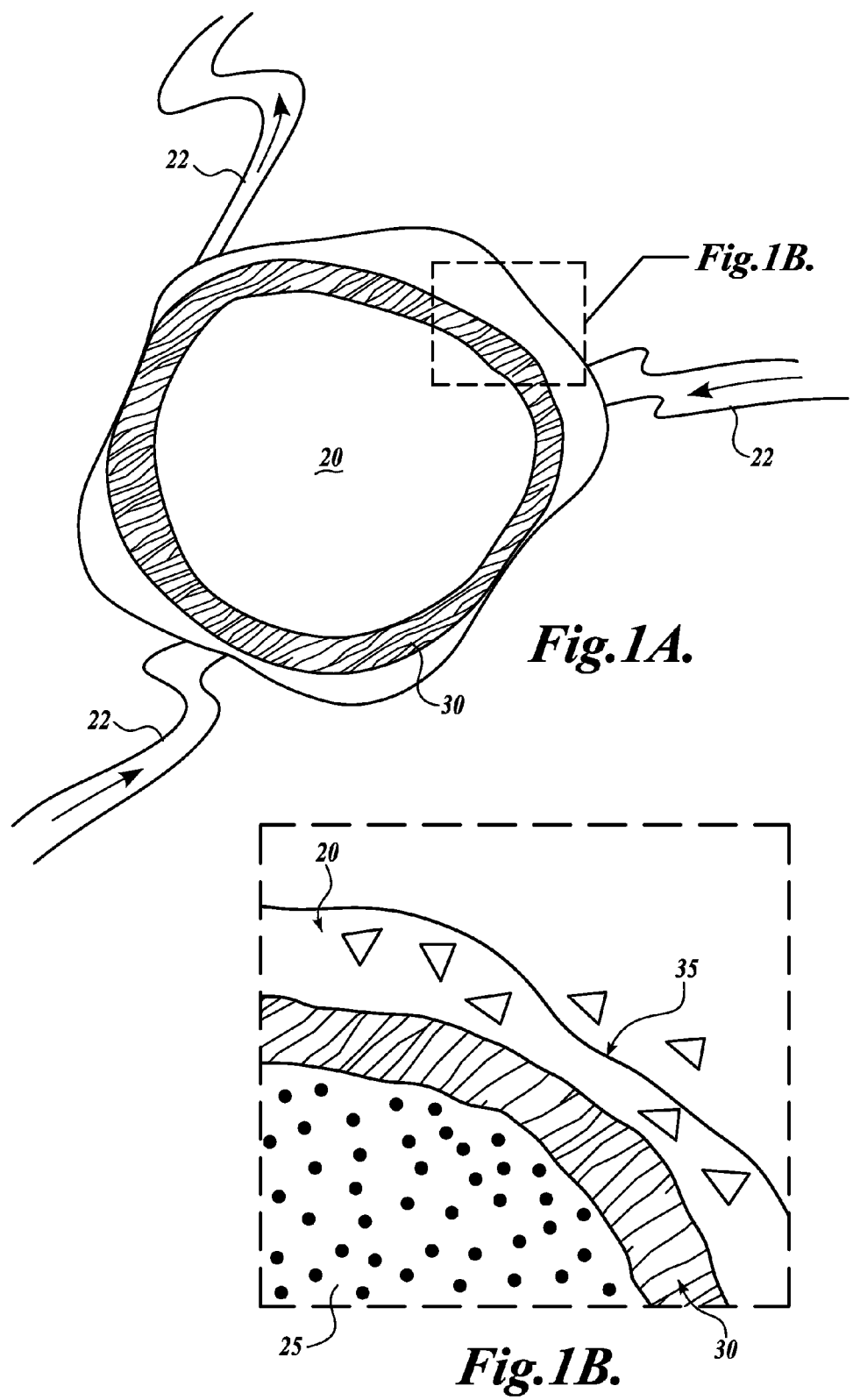
- FIG. 1A shows an internal tissue volume to be surrounded with an ablated shell in accordance with one embodiment of the disclosed technology.
FIG. 1B is a detailed view of tissue inside and outside of the ablated shell.

FIG. 1A illustrates a tissue volume, such as a uterine fibroid 20, to be treated. Uterine fibroids may be irregularly shaped but are often generally spherical or oval shaped. The fibroid 20 includes one or more blood vessels 22 that supply the fibroid 20 with blood. In order to treat the fibroid 20, a 3-dimensional ablated shell 30 is formed inside the periphery of the fibroid 20 in a manner that isolates the fibroid tissue inside the shell from the blood vessels 22 that supply blood to, and take blood from the fibroid 20. By cutting off the interior tissue from its blood supply with the ablated shell 30, this interior tissue can be left in the body to ischemically necrose and eventually be absorbed or healed via normal body healing mechanisms over a period of days/weeks.

In one embodiment, an ablated shell 30 is created by exposing the tissue situated in the shell to HIFU energy for a sufficient time or at sufficient power so as to cause direct tissue necrosis. This is to be distinguished from secondary ischemic necrosis that occurs in the tissue inside the shell as a result of it being cut off from its blood supply or as a result of other effects listed above. Because the volume of tissue ablated to create the shell is smaller than the overall volume of tissue to be treated, the time required to treat the combined mass of tissue (i.e. shell plus encapsulated volume) is reduced below that which would be required if the entire volume were to be directly ablated. As used herein, the term "ablation" refers to the direct necrosis of tissue resulting from the immediate thermal and/or mechanical effects caused by exposure of the tissue to the energy source. Also as used herein, the term "shell" refers to an ablated surface which reduces or eliminates blood flow across that surface. The geometry of this surface may be such that it entirely encapsulates a volume (e.g., a sphere) or non-closed such that it only partially encapsulates the volume (e.g., a concave disk). The term "encapsulate" refers to creation of such surfaces.

In FIG. 1A, the shell 30 is shown as fitting entirely within volume of the fibroid 20. However, the size of the shell may be varied so that its inner non-ablated region encapsulates the entire fibroid 20. Alternatively, the fibroid 20 may have multiple shells created therein.

In another embodiment, one or more partial shells are created which do not entirely encapsulate the tissue site, but reduce or eliminate blood flow to or from its interior across those partial shell(s). This leads to necrosis of at least part of the tissue volume.

FIG. 1B illustrates a close-up view of the interior of the fibroid 20 and the ablated shell 30 that surrounds it. As indicated above, the fibroid 20 includes an interior region 25 within the ablated shell 30 that will ischemically necrose by virtue of the tissue being cut off from an external blood supply (with some contributions via other secondary injury pathway mechanisms associated with healing, e.g., inflammation, apoptosis, et. al.). Tissue that forms the ablated shell 30 is directly necrosed via thermal and/or mechanical effects of exposure to the focal zone of the HIFU beam. Some fibroid tissue 35 external to the ablated shell 30 may also be partially or completely destroyed via thermal necrosis (due to heat conducted from the ablated shell 30) and/or secondary injury pathway mechanisms (ischemia, inflammation, apoptosis, et. al.).

Figure 2:
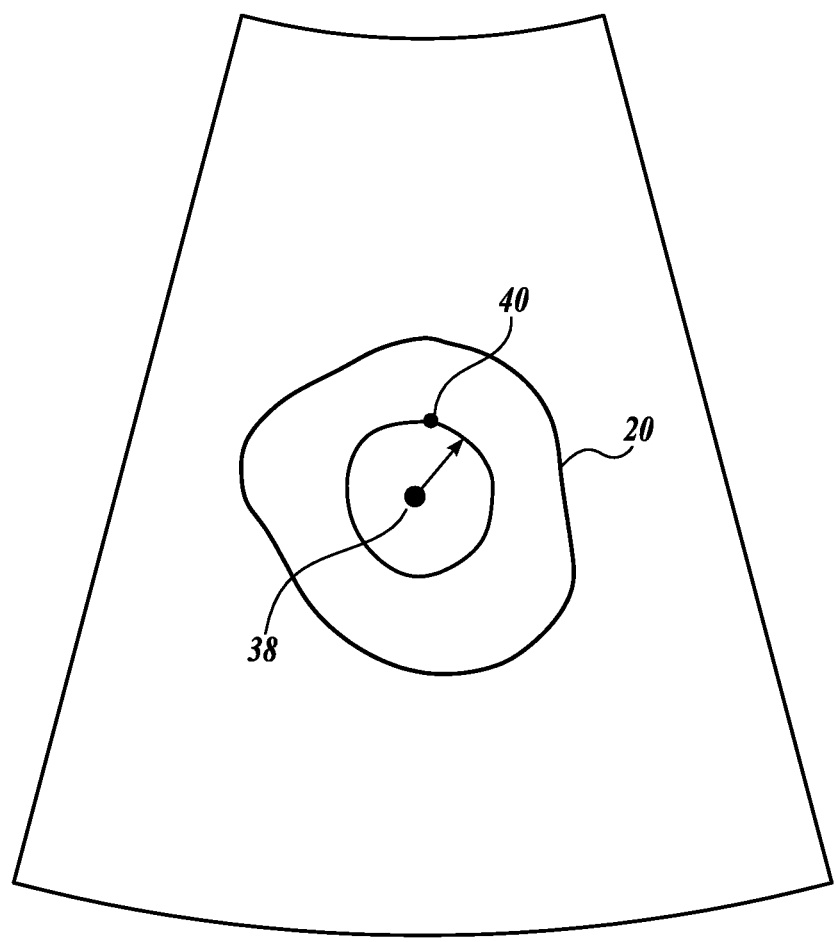
FIG. 2 illustrates an ultrasound image of a uterine fibroid tumor to be treated.

FIG. 2 illustrates a 2-dimensional image of a fibroid 20 produced with an ultrasound imaging transducer and other ultrasound imaging components. As will be explained in further detail below, in one embodiment, an imaging transducer and HIFU transducer are combined as a single unit. In one embodiment, an ultrasound imaging transducer, ultrasound image processor and display (all not shown) are used to produce the image of the fibroid 20 for a physician. The display may include a crosshair or other marker 38 on the image of the fibroid 20 that indicates a reference point with respect to the focal zone of the HIFU transducer so that a user can aim the HIFU transducer at the tissue volume. The physician can interact with the display by, for example, adjusting the radius of a circular marker ring 40 that is centered around the crosshair 38 in order to specify the boundaries of the desired treatment volume or the boundaries of the ablated shell to be created (which may be the same). From the boundaries defined by the size of the marker ring 40, a processing system, such as general or special purpose computer (not shown) computes the size of the ablated shell that should be created to encapsulate the fibroid 20. In some embodiments, the marker ring 40 may be adjustable to form shapes other than a circle, such as ovals or cones, etc., by, for example, stretching the sides of the marker ring 40 in order to allow the physician to define the shape of the three-dimensional ablated shell. In one embodiment, the size of the marker ring 40 is adjusted manually by the physician. In another embodiment, image processing techniques may be used to automatically size the marker ring based on an estimate of the boundaries of the tissue to be treated. The boundaries may be further adjusted by the physician if desired. In some embodiments, the boundaries may be adjusted on a three-dimensional image of the tissue. Once the size of the size of the shell to be created is determined, a computer with the HIFU treatment system begins controlling the position of the focal zone of the HIFU transducer to ablate the tissue to create the shell.

Figure 3A:
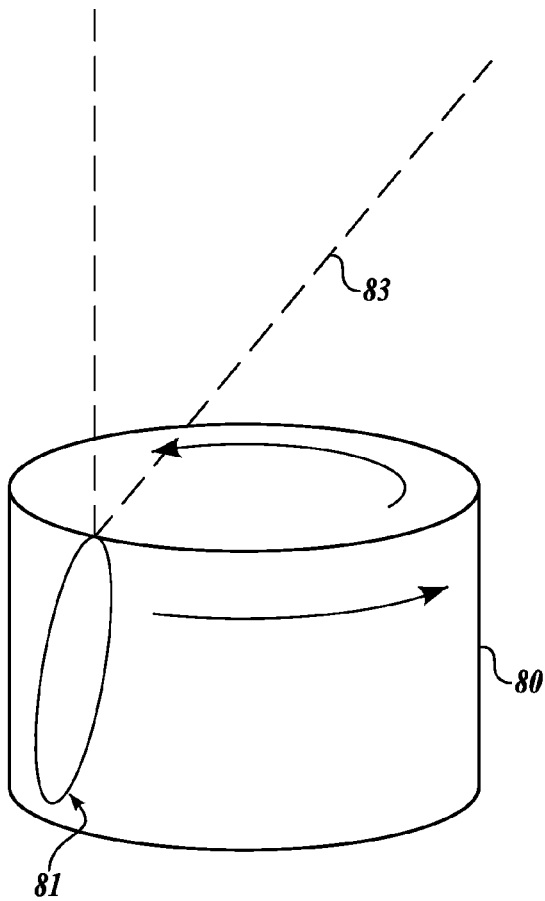
FIGS. 3A and 3B illustrate a cylindrical elemental treatment volume created in accordance with an embodiment of the disclosed technology.
Figure 3B:
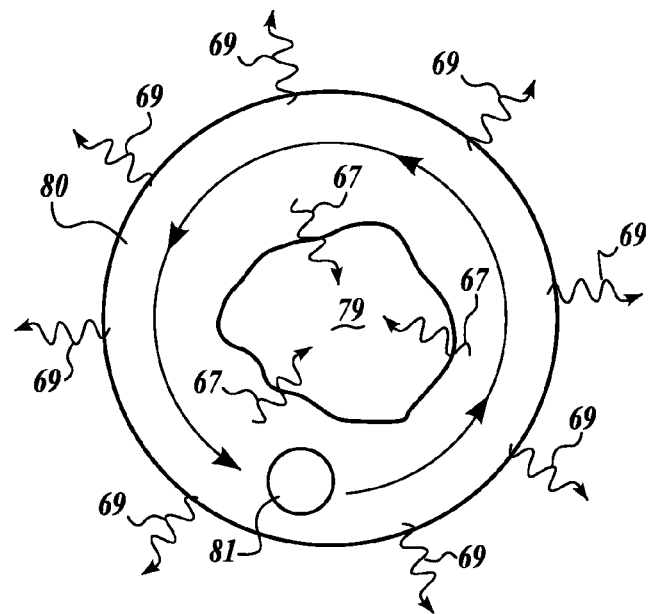

FIGS. 3A and 3B illustrate one exemplary configuration of a cylindrical elemental treatment volume 80 that is used to build up the full desired treatment volume. The elemental treatment volume 80 is created by directing a focal zone 81 of a HIFU beam 83 around the perimeter of the elemental treatment volume. The focal zone 81 can be continuously moved around the perimeter of the elemental treatment volume for one or more times while a HIFU transmitter continually transmits HIFU pulses until the perimeter of the elemental treatment volume 80 is sufficiently ablated. Alternatively, the focal zone 81 can be moved to discrete positions around the perimeter and the HIFU beam 83 pulsed on and off to fully ablate the different positions around the perimeter of the elemental treatment volume.

As shown in FIG. 3B, the elemental treatment volume 80 has a center area 79 that is not directly or is minimally exposed to the focal zone 81 of the HIFU beam 83. This center area 79 is actively necrosed by heat conduction created as the perimeter of the elemental treatment volume is ablated. In one particular preferred embodiment, the elemental treatment volume 80 has a diameter of approximately 11 mm. and a height of approximately 10 mm., thereby producing a volume of approximately 1 cc. In this particular preferred embodiment, the volume of the elemental treatment volume is therefore approximately 40 times greater than the volume of the focal zone. Heat from the ablation of the perimeter of the elemental treatment volume is conducted inwards as indicated by the arrows 67 in order to treat the center area 79. At the exterior of the elemental treatment volume, the heat is dissipated outwards as indicated by the arrows 69.

Figure 3C:
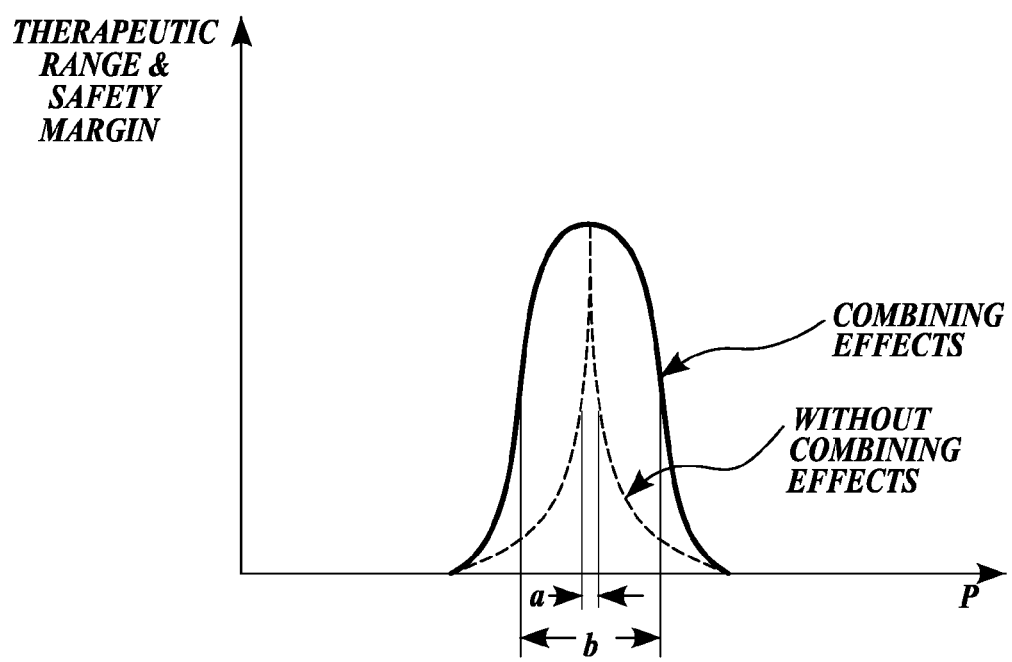
FIG. 3C illustrates a relationship between safety and therapeutic range versus applied power of a HIFU signal.

FIG. 3C conceptualizes the effect of the applied HIFU power level on the resultant therapeutic range and safety margin of a HIFU treatment regimen. With conventional techniques that do not combine the effects of the technology disclosed herein, the range of acoustic power levels where a treatment regimen is both effective and safe can be relatively narrow, as indicated by range "a". That is, small changes to the HIFU power that result in it falling outside the narrow region "a" make the treatment ineffective or possibly unsafe. However, by treating the target tissue using a combined set of effects including one or more of the following (1) focal scanning to produce elemental treatment volumes, (2) inward heat conduction within an elemental volume, and (3) spatial specificity resulting from the application of highly nonlinear acoustic energy with a moderately low fundamental frequency, it is believed that the range of safe and efficacious HIFU power levels can be increased, as indicated by range "b," such that the treatment method is not as sensitive to changes in HIFU power delivered. These various effects acting synergistically to improve HIFU treatment efficiency and collateral tissue safety will be more fully described below.

Figure 3D:
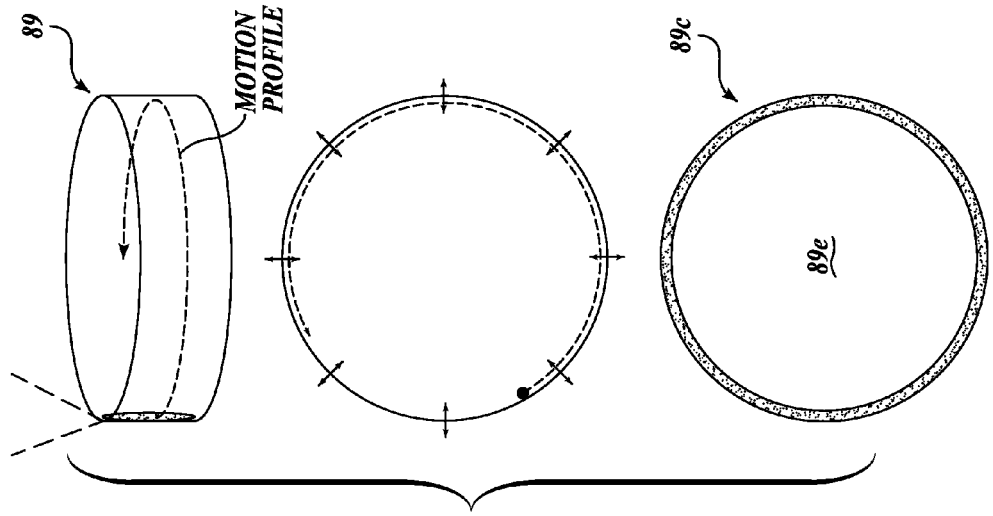
FIG. 3D illustrates the side and top views of an elemental treatment volume that is created in accordance with one embodiment of the disclosed technology, as well as the completely filled-in ablation volume produced by this embodiment.

The size of the elemental treatment volumes can be varied as a function of a variety of factors including the geometry of the devices that will apply the treatment energy. In the embodiment shown in FIG. 3D, an elemental treatment volume 80 is shown in top and side views. This elemental treatment volume is generally cylindrical with a width W and length L that are both approximately equal to the length of the focal zone of the HIFU transducer. As the focal zone is moved around the perimeter of the elemental treatment volume with velocity V, the entire cross-section 80a of the elemental treatment volume is treated due to either direct exposure to the HIFU beam or indirect thermal necrosis caused by inward conduction of heat from the treated perimeter.

Figure 3E:
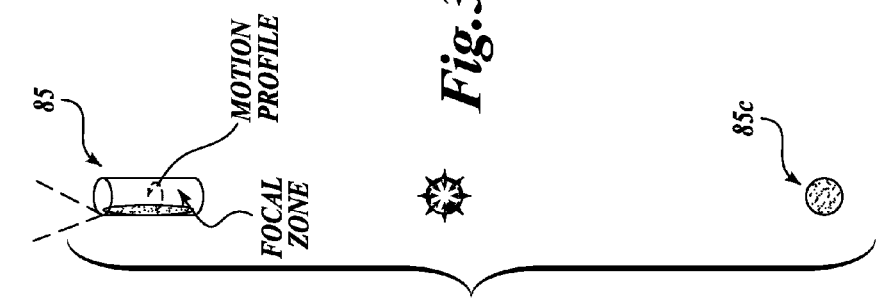
FIG. 3E illustrates the side and top views of a smaller elemental treatment volume that is created in accordance with another embodiment of the disclosed technology, as well as the completely filled-in ablation volume produced by this embodiment.

FIG. 3E shows top and side views of a smaller elemental treatment volume 85 having a diameter that is approximately twice the diameter of the focal zone. With this embodiment, the elemental treatment volume still has well defined boundaries due to the motion of the focal zone around the perimeter of the elemental treatment volume as it is being created. The elemental treatment volume has a cross section 85a that is generally uniformly treated all the way through the interior of the volume. The disadvantage of this elemental treatment volume 85 is that it is small compared with the elemental treatment volume shown in FIG. 3D, and therefore more elemental treatment volumes may be required to treat a desired tissue site.

Figure 3F:
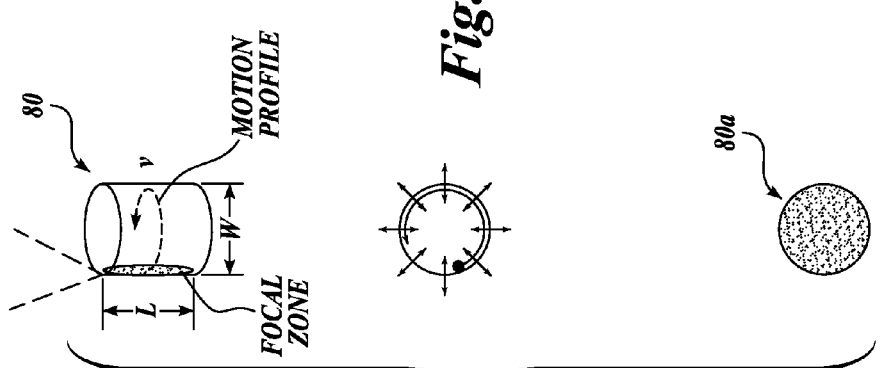
FIG. 3F illustrates the side and top views of a larger elemental treatment volume that is created in accordance with another embodiment of the disclosed technology, as well as the partially filled-in ablation volume produced by this embodiment.

FIG. 3F shows top and side views of yet another elemental treatment volume 89 having a diameter that is significantly larger than the focal zone of the HIFU transducer. In this case, cooperative heating of the interior of the elemental treatment volume does not occur and only the perimeter 89c of the elemental treatment volume is ablated. As a result, the interior may not be treated, as depicted by the open center within the ablated ring. While the geometry of the elemental treatment volume 89 is not currently preferred for creating the building blocks used to treat a volume of tissue, the geometry may be useful in creating ablated shells around tissue treatment sites as will be discussed in further detail below. In yet another embodiment, the building blocks (elemental treatment volumes) may be formed of linear segments created by passing the beam for a number of times along their length.

FIG. 3G illustrates a scenario in which the entire dose of treatment energy is applied to the tissue in a single pass of the HIFU focal zone along or around the elemental volume. Rapid deposition of energy in this manner can result in the formation of large pre-focal bubbles in the tissue that reflect the treatment energy, therefore preventing even ablation at all depths along or around the elemental volume. As a result, an uneven or "ragged" treatment pattern 91a is created, having different depths of treated tissue. In contrast, by distributing the dose of treatment energy over a series of passes along or around the elemental volume, a more even and uniform treatment pattern 91b is created, such as shown in FIG. 3H. On each pass, a portion of the elemental treatment volume is ablated and the elemental treatment begins to build up. The multi-pass technique is used in the creation of the elemental treatment volumes described below.

FIG. 3I illustrates a technique for creating another embodiment of an elemental treatment volume with an arc or segment-type geometry. This elemental treatment volume can be used to create rings or other shapes with uniform treatment depths and in one method to form a shell around the desired treatment volume. In this embodiment, the focal zone of the HIFU transducer is moved back and forth over a portion (e.g. an arc) of the perimeter. The back-and-forth motion of the HIFU focus results in tissue ablation at uniform depths because it distributes the acoustic energy over a broader region during the treatment, therefore preventing the formation of large pre-focal bubbles that can reflect energy and result in uneven or "ragged" treatment patterns. Multiple treated arcs can therefore be created side by side to complete the treated perimeter of the desired treatment volume.

In each of the examples shown in FIGS. 3A-3B, 3D-3I, the elemental treatment volumes have a height or length that is approximately the same as the focal zone of the HIFU transducer. In some embodiments, the height of an elemental treatment volume may be increased by varying the depth of the focal zone during the application of treatment energy.

In one embodiment described in further detail below, the focal zone 81 of the HIFU beam 83 is steered over the perimeter of the cylindrical elemental treatment volume 80 with a mechanical wobbler at a rate that acts to largely confine the heat within the center 79 of the treatment volume as the elemental treatment volume is being created. The focal zone of the HIFU signal is directed around the perimeter of the elemental treatment volume in such a manner that the interior of the treatment volume is ablated by inward thermal conduction, but the energy deposited beyond its exterior boundary remains below the threshold required for inciting thermal or mechanical damage. Alternatively, the focal zone 81 of the HIFU beam 83 can be steered around the perimeter of the elemental treatment volume with electronic beam steering.

Figure 8:
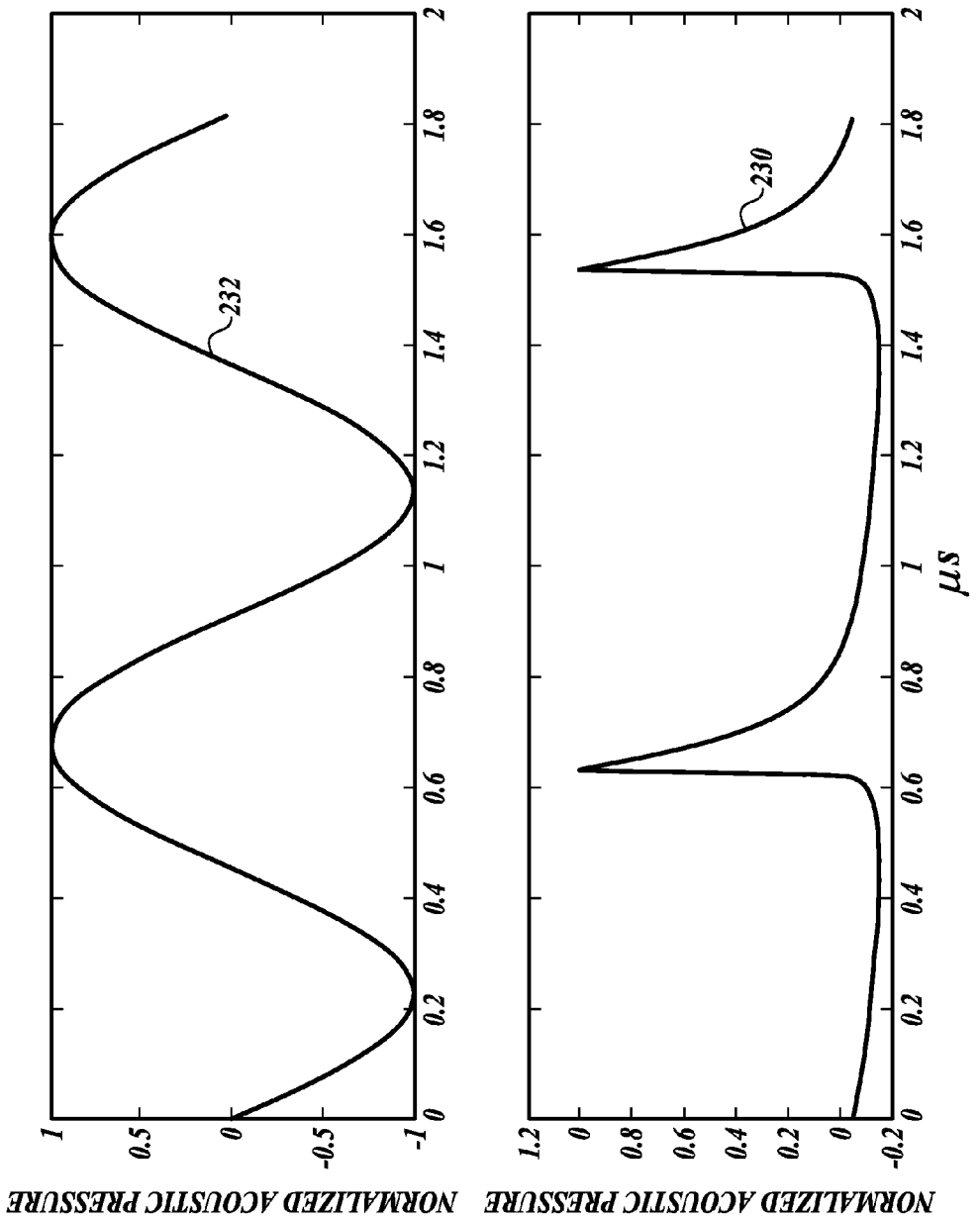
FIG. 8 illustrates two different HIFU signal waveforms.

To create the elemental treatment volumes described herein, a substantially non-linear, pulsed waveform of HIFU energy, such as the waveform 230 shown in FIG. 8 is applied to the perimeter of the elemental treatment volume. The currently preferred embodiment of this elemental unit volume technique relies on the HIFU treatment waveform being substantially nonlinear in nature, meaning that the originally sinusoidal characteristic of the incident waveform is heavily distorted by the time it reaches the HIFU focus. The presence of nonlinearity in the focal acoustic waveform is indicative of the conversion of energy from the fundamental acoustic frequency into higher harmonics, which in turn are more readily absorbed by the tissue residing in and immediately adjacent to the focal zone. This effect results in a dramatically increased heating rate that remains tightly localized to the focal region, leading to increased treatment efficacy while maintaining the safety of collateral tissues. The degree of focal waveform nonlinearity required in this preferred embodiment ranges from moderate distortion, where the compressional pressure is perhaps twice that of the rarefactional pressure, to severe distortion reaching the point of shock formation, where the compressional pressure can be more than five times greater than the rarefactional pressure.

In one particular experimental construct, the peak acoustic powers used to attain the desired level of nonlinearity in the HIFU focal zone range from 800-1700 watts, depending upon the depth of the particular elemental tissue volume with respect to the body surface. These acoustic powers are delivered to the elemental volume in a pulsed fashion, where pulses consist of 15-30 cycles at a nominal operating frequency of 1 MHz and are delivered at pulse repetition frequencies (PRFs) of 4-8 kHz, resulting in a pulsing duty factor of approximately 10%. This pulsing duty factor is reduced to an overall duty factor of approximately 5% through the use of interleaved ultrasound imaging during the HIFU treatment (as described in U.S. Pat. No. 6,425,867, which is herein incorporated by reference). While the HIFU transmitter is applying energy of these specifications, a cylindrical elemental treatment volume is created by mechanically wobbling the HIFU focus, which is approximately 10 mm. in length and 2 mm. in width in FWHM dimensions, around a 10-mm-diameter trajectory at a rate of approximately 2 Hz. In this case, the diameter around which the HIFU focus rotates is approximately equal to the HIFU focal zone length and five-fold greater than the HIFU focal zone width. The mechanical wobbling and HIFU treatment continue for a total time of 10-50 seconds per elemental volume, depending on the depth in the tissue where the elemental volume is located and the overall tissue treatment volume desired.

Although the currently preferred embodiment uses a non-linear pulsed waveform, it will be appreciated that a continuous-wave (CW) or linear HIFU signal such as the waveform 232 shown in FIG. 8 may also be used depending on the power level used and the rate at which the focal zone is moved.

Though this previous example specifies the use of a 2 Hz mechanical rotation rate around the perimeter of the elemental volume, both lower and higher rates could be used to ablate these types of elemental volumes. However, if too low a rate is used, the heat that ablates the perimeter of the elemental treatment volume may not be sufficiently contained within the interior of the elemental volume and may result in adverse effects in collateral tissues. Higher rotation rates may require the use of an electronic beam former instead of mechanical rotation and may also affect the HIFU treatment power necessary. In one embodiment, the mechanical rotation rate of the HIFU focus about the unit volume diameter is at least 0.25 Hz. In another more preferred embodiment, this rotation rate is at least 1 Hz, while in the most preferred embodiment this rate is at least 2 Hz. Regardless of the rotation rate used, it is preferable to apply energy over a number of passes (e.g. two or more) around the perimeter at a rate and power level that allows the entire elemental treatment volume to be ablated in unison, in order to achieve symmetric geometry in the shape of the ablated elemental volume and prevent distortion to produce an evenly ablated tissue site.

As will be appreciated, the size of the elemental treatment volume is preferably selected so that a center region 79 can be indirectly treated while not unduly increasing the treatment time required to treat a desired volume of tissue. If the size of the elemental treatment volume is too large, the center region 79 will not be ablated by effective conduction of heat into the interior of the volume. Conversely, if the size of the elemental treatment volume is too small, then the time required to treat the desired treatment volume must be adjusted to avoid overdosing the elemental volume and potentially causing damage to collateral tissues. In addition, the time to create each elemental treatment volume may decrease as the focal zone is moved proximally toward the surface of the body, due to the residual heat persisting in the treatment volume from ablation of the more distal elemental volumes.

Although the elemental treatment volume 80 shown in FIGS. 3A and 3B is cylindrical in shape, it will be appreciated that other shapes such as spherical or cubic elemental treatment volumes etc. could be created depending on the steering capabilities of the HIFU beam 83.

In a currently preferred embodiment, the method of creating the elemental treatment volumes takes advantage of several features of HIFU therapy resulting from the synergistic effects of highly-nonlinear acoustic waveforms and the mechanical or electronic motion of the HIFU focus about the perimeter of the unit volume. These combined effects comprise a set of operating points that result in the enhanced safety and efficacy observed when using this treatment method. This set of operating points includes a combination of the following: (1) The elemental treatment volume is ablated in such a way that the interior region is primarily destroyed through inward conduction of heat, not direct ablation by HIFU. This feature enlarges the size of the elemental volume without increasing the HIFU dose that has to be delivered to the tissue to do so. (2) The motion of the HIFU focal zone about the elemental treatment volume perimeter is accomplished by making multiple passes around the perimeter using a specified rotation rate, as opposed to making one a single pass around the circumference of the unit volume to achieve ablation. This feature allows the tissue within the elemental treatment volume to be ablated with uniform, smooth boundaries and equal length at substantially all points around the perimeter. (3) The elemental treatment volume is subjected to highly concentrated acoustic energy only in the focal region of the HIFU beam by virtue of the use of a highly nonlinear acoustic waveform that dramatically enhances the heating rate in the focal zone. (4) The fundamental acoustic frequency of the HIFU applicator is kept low enough to ensure safe propagation through collateral tissues proximal to the body surface.

Figure 3J:
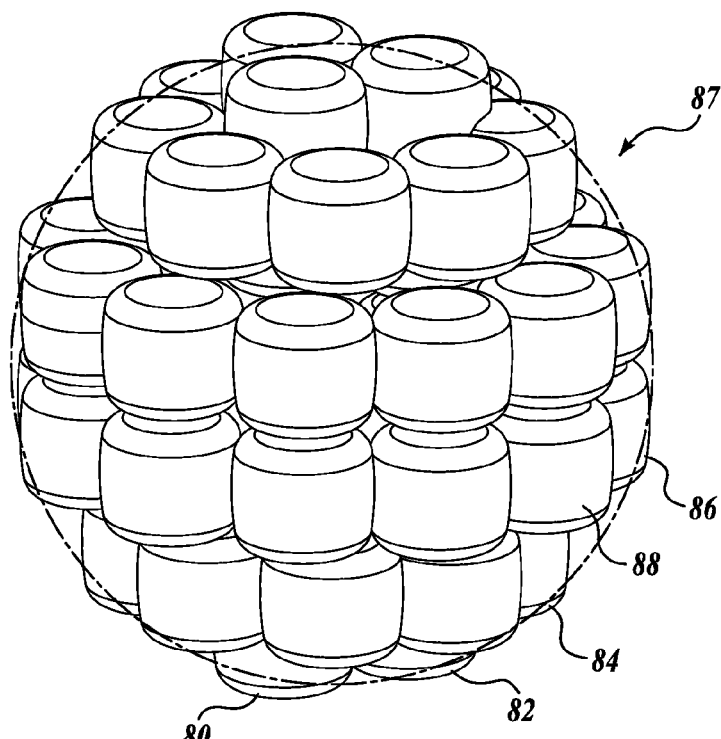
FIGS. 3J and 3K illustrate a technique for creating an ablated shell around a tissue volume from a number of elemental treatment volumes in accordance with an embodiment of the disclosed technology.
Figure 3K:
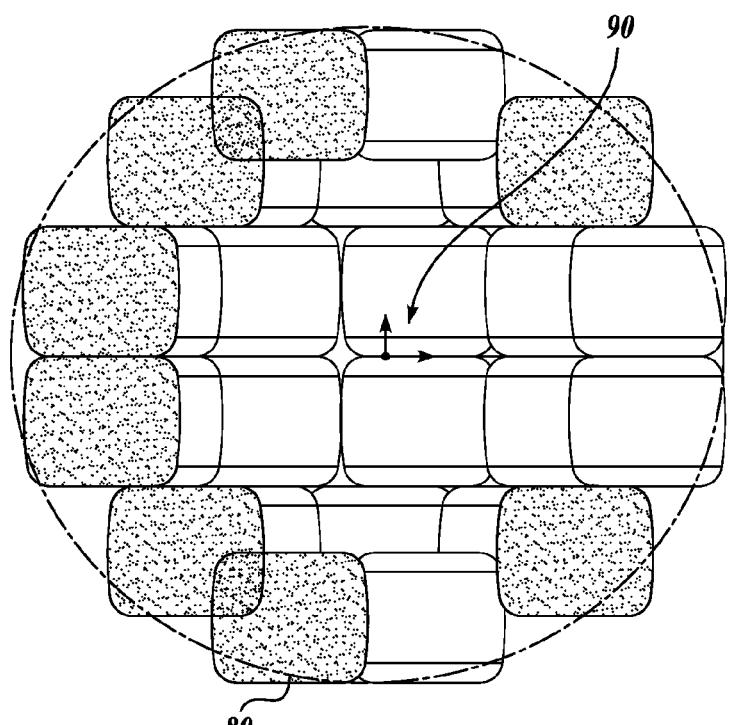

FIGS. 3J and 3K illustrate one technique for using the elemental treatment volumes 80 to treat a desired volume of tissue. In this embodiment a three dimensional pattern of adjacent elemental treatment volumes are created such that together they form an ablated shell that surrounds all or a portion of a desired tissue treatment volume. In the embodiment shown in FIGS. 3J and 3K, an ablated shell 87 is formed from a number of smaller ablated elemental treatment volumes 80, 82, 84, 86, 88 etc. Each of the elemental treatment volumes is created sufficiently close together to form a necrosed shell or barrier of ablated tissue between the encapsulated tissue and its blood supply. As shown, the elemental treatment volumes 80, 82, 84, 86, 88 etc. are created adjacent to each other in annular patterns of increasing internal diameter that extend from the distal end of the desired tissue treatment volume to approximately midway in the tissue volume, where the diameter of the treatment volume is the largest. The diameter of the annular patterns then progressively decreases towards the proximal end of the tissue volume to be treated. Together the annular patterns create a shell with a "hollow" interior space 90 that encapsulates a portion of the desired tissue volume to be treated. With the elemental treatment volumes placed sufficiently close to each other, blood supplied to the fibroid or other tissue to be treated is cut off, or is substantially reduced so that the tissue will ischemically necrose when left in the body. In addition, some or all of the tissue within the center of the shell may necrose due to heat conduction when the shell is being created. Because the entire treatment volume is not ablated, there is less possibility that excess heat will be created in the body which may damage untargeted tissue and the treatment time is significantly reduced from that required if the entire volume were to be directly ablated.

Although the shell 87 illustrated in FIGS. 3J and 3K is shown as being hollow, it will be appreciated that it in some circumstances it may be desirable to create one or more elemental treatment volumes within the interior of the shell to actively necrose some or all of the tissue inside the shell 87. The number and spacing of the elemental treatment volumes can be decided by the physician based on experience, the time available for treatment, the type of tissue being treated or other factors. Alternatively, a processor can be programmed to determine if the interior of the shell should be empty or filled with one or more elemental treatment volumes.

The shell 87 is shown in FIG. 3J as being substantially sealed about its outer surface. However, it will be appreciated that a shell 87 can still be created even if there are gaps between the individual elemental treatment volumes. How close the elemental treatment volumes are placed in order to create the shell may be based on the type of tissue being treated, the thermal conductivity of the tissue, its absorption characteristics, or other factors.

As will be appreciated, other patterns besides shells of elemental treatment volumes can be used to treat the desired tissue volume. For example, layers of horizontally spaced adjacent elemental treatment volumes can be created in the desired tissue volume. The distance between elemental treatment volumes in a layer can be closely spaced or more spread apart.

Figure 4A:
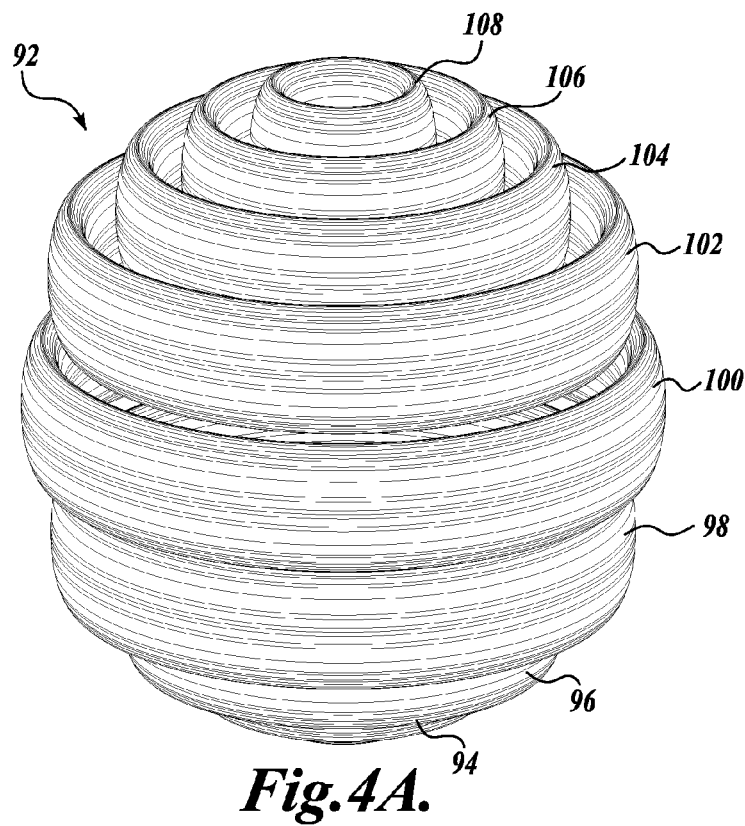
FIGS. 4A and 4B illustrate a second technique for creating an ablated shell around a tissue volume in accordance with another embodiment of the disclosed technology.
Figure 4B:
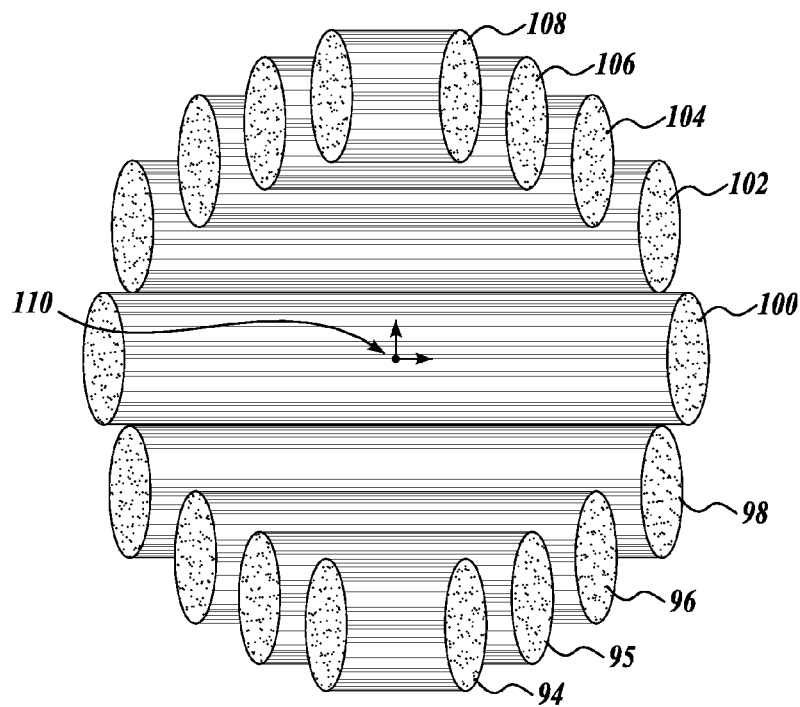

FIGS. 4A-4B show an alternative technique for creating an ablated shell 92 around a tissue volume in accordance with the disclosed technology. In this embodiment, an ablated shell comprises a stacked series of toroids, each having a varying internal diameter. A toroid 94 of minimum internal diameter (or a solid disk) is placed at the distal end of the tissue to be treated with respect to the HIFU transducer. Additional toroids are created proximally to the distal toroid 94, including toroids 95, 96, 98 of increasing diameter up to a toroid 100 where the toroid has a maximum internal diameter. The internal diameters of the toroids then get progressively smaller with toroids 102, 104, 106 as the HIFU focal zone is moved more proximally before closing the shell 92 with a toroid 108 of minimum internal diameter (or a solid disk) at the most proximal location in the treatment volume. As can be seen in FIG. 4B, the interior of each of the toroids 94-108, when stacked, define a shell with a "hollow" (i.e. un-ablated) region 110 that encapsulates a volume of the tissue to be treated and isolates it from its blood supply. In one embodiment, the outer diameter of the toroids 94-108 is selected to correspond to the outer dimension of the fibroid in order to minimize the volume of tissue that is directly ablated with HIFU. In another embodiment, the outer diameters of the toroids 92-106 are selected to be within a set distance internal to the fibroid's outer boundary in order to allow the fibroid tissue external to the ablated shell 92 to be partially or completely destroyed via thermal necrosis (due to heat conducted from the ablated shell 92) and/or secondary injury pathway mechanisms (ischemia, inflammation, apoptosis, et. al.). In yet another embodiment, the inner diameters of the toroids 94-108 correspond to the outer diameter of the tissue volume such that the interior 110 of the ablated shell 92 created is slightly larger than the tissue volume, perhaps allowing a more complete kill of tumor tissue at the expense of killing a small amount of surrounding healthy myometrium. Another advantage of such an embodiment is the ability to create the ablated shell 92 such that it overlaps the endometrial lining, thus necrosing at least some of the nearby endometrium which may reduce menorrhagia symptoms.

Figure 4C:
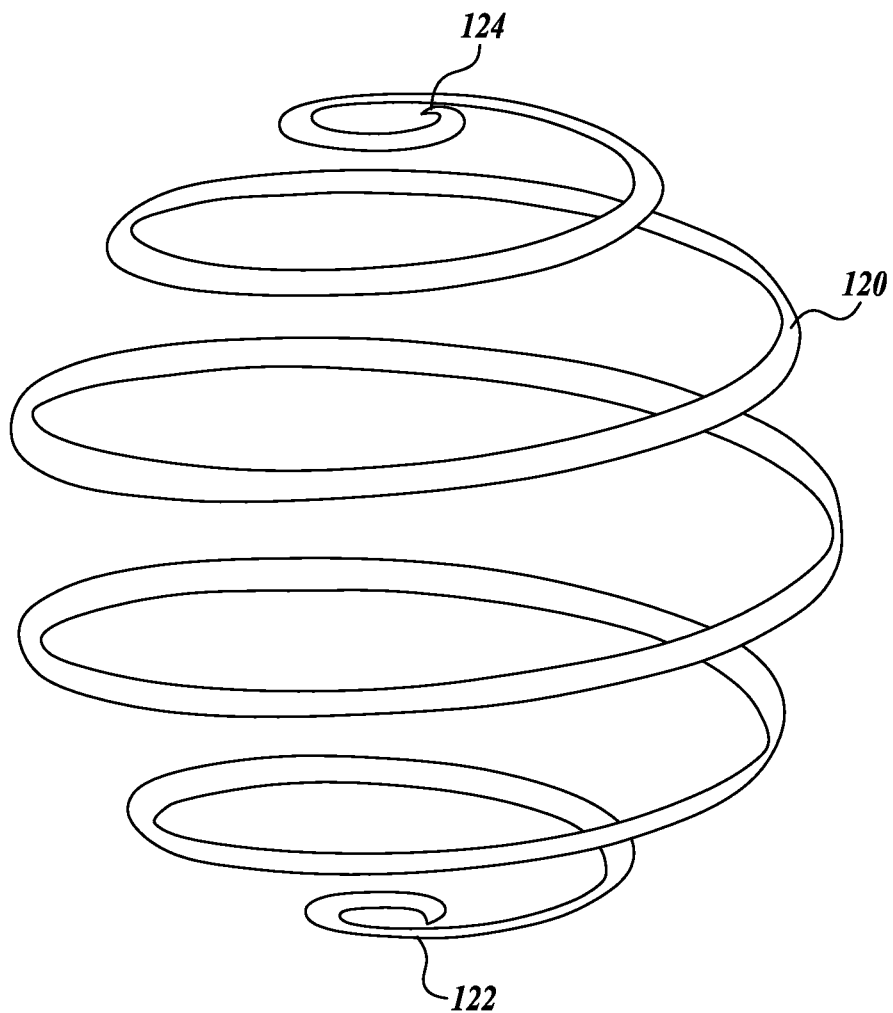
FIG. 4C illustrates a third technique for creating an ablated shell around a tissue volume in accordance with another embodiment of the disclosed technology.

FIG. 4C shows yet another embodiment of an ablation pattern that creates an ablated shell to encapsulate a tissue volume and isolate it from an external blood supply. In the embodiment shown, an ablated shell is created from a spiral pattern 120. The spiral has a minimum diameter at a distal end 122 of the tissue volume to be treated, expands to a maximum diameter at approximately the mid point of the tissue volume, and then progressively decreases in diameter towards the proximal end 124 of the tissue volume. Each loop of the spiral pattern 120 is sufficiently close to an adjacent loop that the tissue is actively necrosed in order to create an ablated shell around a tissue volume that cuts off the tissue in the shell from its blood supply. As will be appreciated, the spiral pattern 120 could also be used to create the smaller elemental treatment volumes described above and shown in FIGS. 3A and 3B depending on the size of the focal zone of the HIFU transducer and the desired size of the elemental treatment volumes.

Figure 4D:
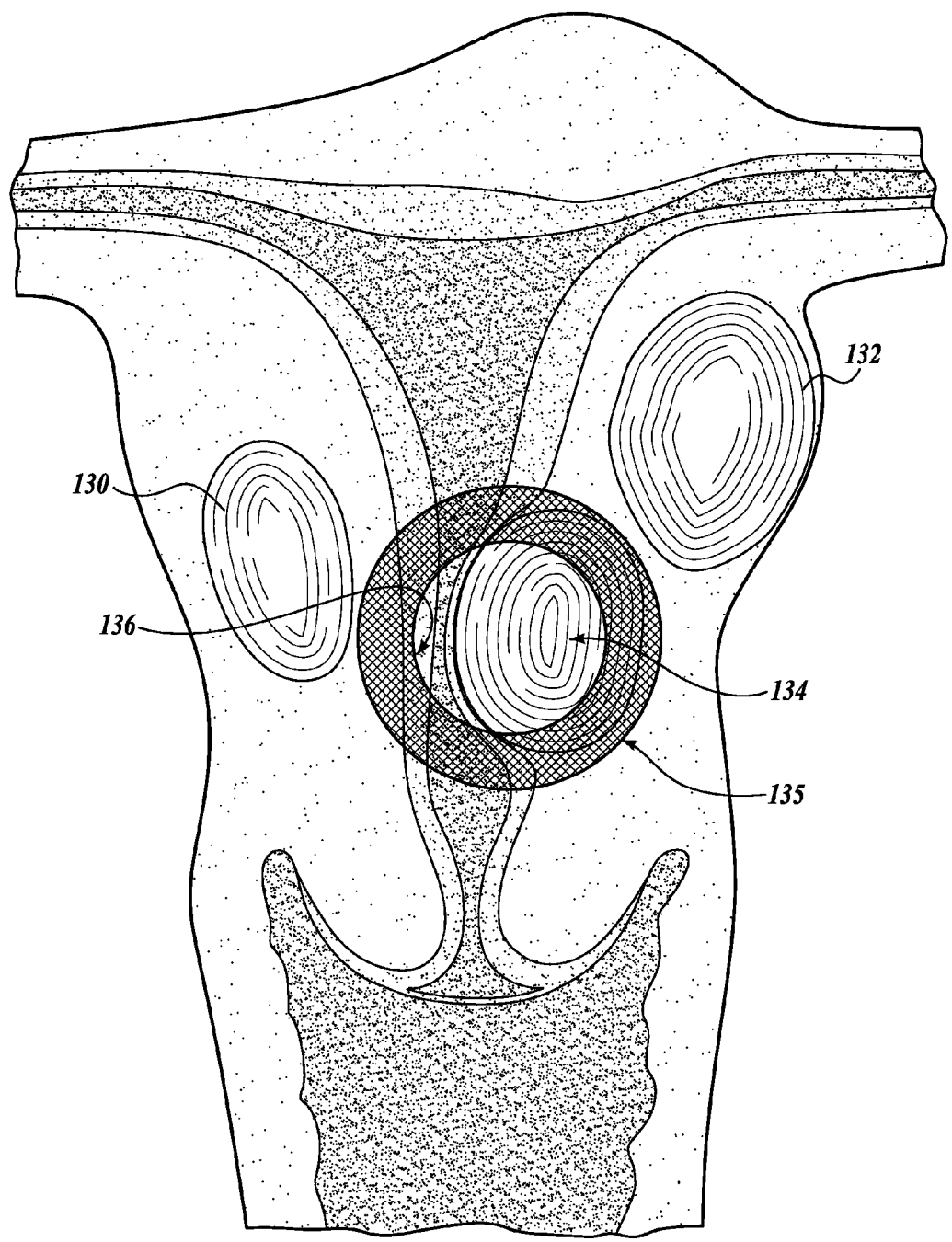
FIG. 4D illustrates a technique for creating an ablated shell around a uterine fibroid, which overlaps at least a portion of the adjacent endometrium, so as to further reduce menorrhagia symptoms.

FIG. 4D illustrates a uterus having three different types of fibroids including an intramural fibroid 130, a subserosal fibroid 132, and a submucosal fibroid 134. In the example shown, an ablated shell 135 is created to encapsulate the entire submucosal fibroid 134 on one side of the uterine wall as well as a portion of the nearby endometrium tissue 136 on the opposite uterine wall. By creating the ablated shell 135 to encapsulate not only the fibroid 134 but also a portion of the adjacent endometrium 136, menorrhagia symptoms may be reduced.

Although the shape of the ablated shells is shown as being generally spherical in FIGS. 3J-3K, 4A-4B and 4C, it will be appreciated that other shapes, such as conical or double conical, ovoid (e.g., egg shaped), or rectangular could be used. The particular shape of the shell created may depend on the shape of the tissue volume to be treated and the ability of the equipment used to steer the focal zone of the HIFU transducer in a desired pattern. Any shell shape of ablated tissue that forms a barrier between tissue internal to the shell and its external blood supply will function to allow the encapsulated tissue to ischemically necrose when left in the body. It will also be appreciated that, as an alternative to ablating an excessively large or irregularly shaped shell, one could ablate two or more regularly-shaped shells adjacent to each other to treat most or all of the desired volume (e.g., 2 spherical shells could be ablated side-by-side inside an oblong tumor, rather than ablating one oblong shell). If numerous shells are created within the tissue volume, one can also form a matrix (or "honeycomb") of ablated elemental tissue volumes with interspersed regions of un-ablated tissue which subsequently ischemically necrose in situ. Such a matrix could involve regular or random spacing of ablated elemental treatment volumes to accomplish the same effect, and the matrix could consist of numerous closed shells (e.g., spherical shells) or layers of stacked/overlapping elemental treatment volumes.

Those skilled in the art will readily appreciate that other advantages of the shell ablation approach are (1) increased treatment rate, since energy is applied to a sub-volume of the tissue ultimately treated, (2) a larger treatment size for a given allotment of treatment time, (3) and less energy required, compared to that which would be used if the entire volume including its interior were directly ablated. Automating a HIFU system to ablate a symmetrical (e.g., spherical) shell will reduce demands on a user with regard to imaging, targeting and probe manipulation. If shell is symmetrical, user can easily visualize its projected relationship to tumor boundaries as visualized with an imaging mechanism such as an ultrasound imager, MRI, x-ray, etc. The user need only manipulate the HIFU system so as to center an overlay of the projected shell within the image of the target tissue, expand the diameter of the shell to desired dimensions (e.g., just inside periphery of the tumor), and then hold the system stationary while the system automatically ablates the specified shell pattern.

Figure 5:
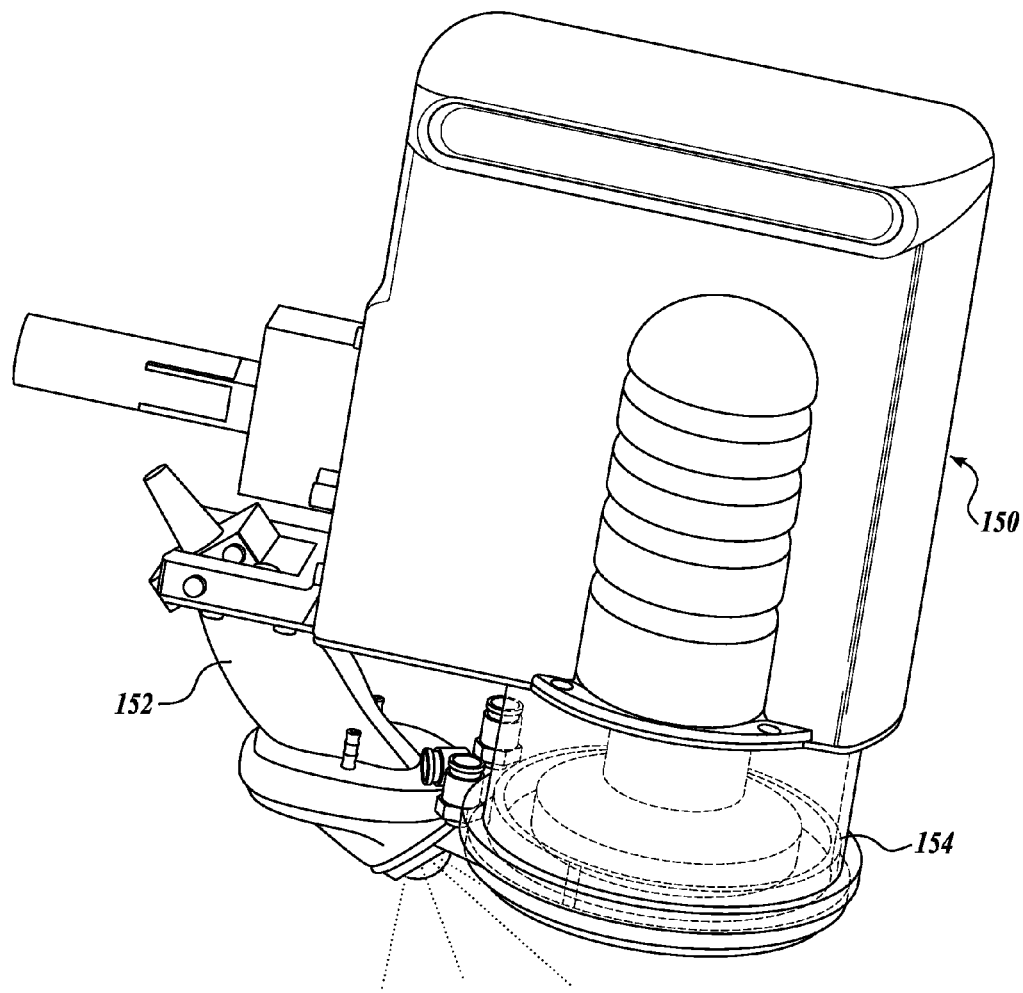
FIG. 5 illustrates a HIFU treatment device in accordance with one embodiment of the disclosed technology.

FIG. 5 shows one embodiment of a HIFU treatment device that can be used to treat tissue in the manner described above. The HIFU treatment device 150 is a hand held or hand guided applicator device that includes an imaging transducer 152 and a HIFU transducer 154. The imaging transducer 152 is fixed in position to capture images of tissue within a body that includes the focal zone of the HIFU transducer 154. As will be explained in further detail below, the focal zone of the HIFU transducer 154 can be mechanically and/or electrically steered to ablate a number of elemental treatment volumes that are adjacently positioned to create a shell that surrounds or encapsulates a desired tissue volume or to create another pattern. While holding the treatment device 150 steady at the desired location, as determined from an image produced from signals obtained from the imaging transducer 152, the focal zone of the HIFU transducer 154 is moved in such a way as to ablate a pattern of elemental treatment volumes in order to create a shell around the treatment volume or to create another pattern of elemental treatment volumes.

The treatment device 150 is coupleable to other components of the treatment system including an image processor and display required to operate the imaging transducer 152 and produce images of the tissue volume. A signal source required to drive the HIFU transducer and a computer to orient the focal zone of the HIFU transducer in a pattern to create the elemental treatment volumes in a desired pattern such as a shell around the tissue volume are also included.

Figure 6:
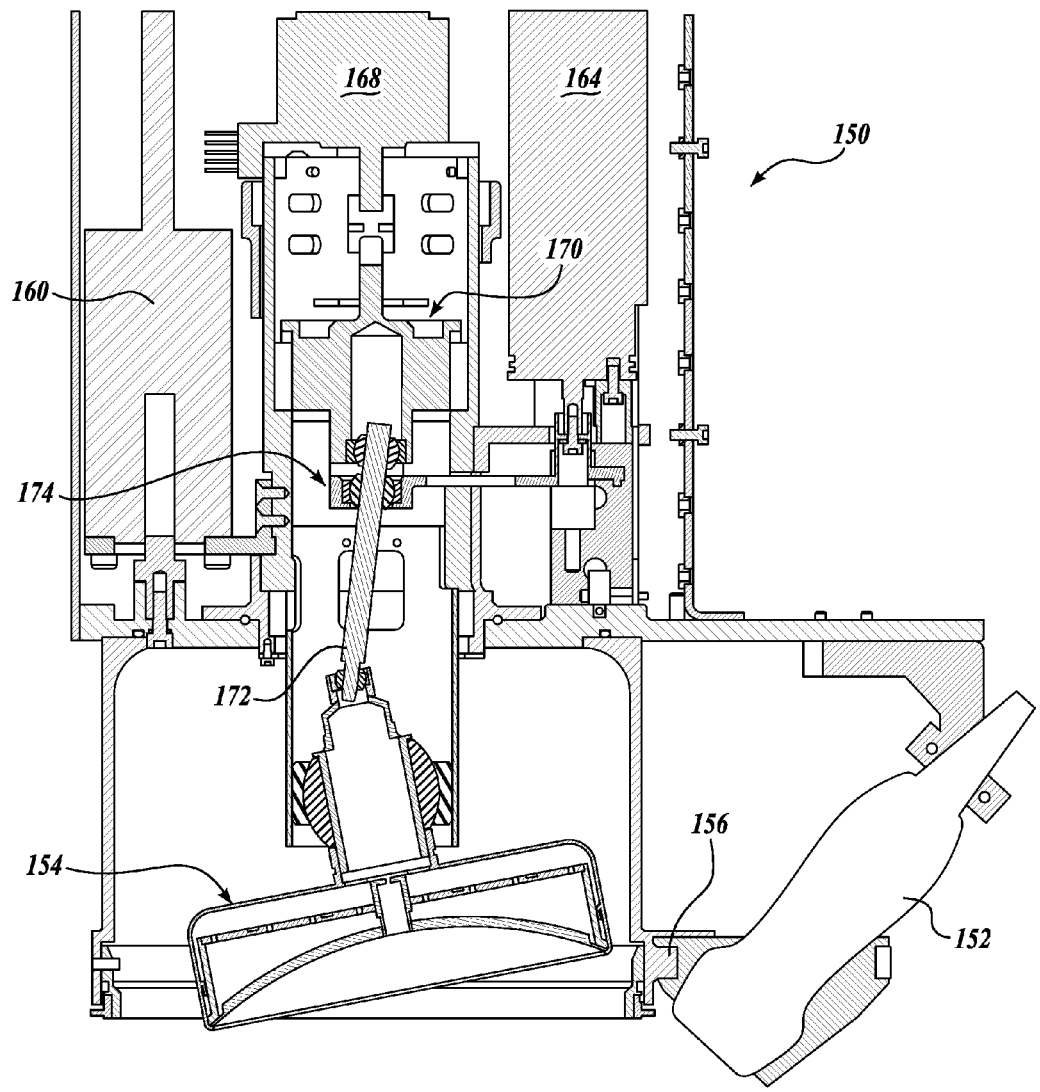
FIG. 6 illustrates one mechanism for varying a position and orientation of a focal zone of a HIFU transducer in accordance with one embodiment of the disclosed technology.

FIG. 6 illustrates one embodiment of a more detailed mechanism for treating the internal body tissues with HIFU signals to create a series of elemental treatment volumes in a shell or other pattern. The treatment device 150 includes a HIFU transducer 154. In the embodiment shown, the HIFU transducer 154 has a fixed focal zone, as defined by the curvature of the piezoelectric elements that comprise the transducer head. A flexible membrane that does not significantly reflect HIFU signals is positioned in front of the HIFU transducer to form a chamber in which liquid can be introduced, stored, and/or circulated. A liquid such as water or de-gassed water then fills the liquid chamber and surrounds the transducer 154 to serve as an acoustic couplant to the tissue. A port 156 connects the treatment device to a pump to allow the liquid of a constant volume to flow around the HIFU transducer.

To adjust the depth of the focal zone where the HIFU signals are delivered to the patient, a linear actuator 160 or motor raises or lowers the HIFU transducer 154 within a housing of the treatment device 150 via a threaded rod or other mechanism. By adjusting the height of the transducer 154 within the housing, the depth where the HIFU signals are delivered within the body can be controlled.

In addition, the treatment device 150 includes an offset bearing 170 that, when rotated by a motor 168, wobbles an end of a shaft 172 around the center of the offset bearing 170. The HIFU transducer 154 is coupled to the other end of the shaft 172 through a slidable bearing. A linear actuator 164 or motor positions a spherical bearing 174 that surrounds the shaft 172 towards or away from the offset bearing 170. The position of the spherical bearing 174 on the shaft 172 controls the angular orientation of the focal zone of the HIFU transducer 154.

Figure 6A:
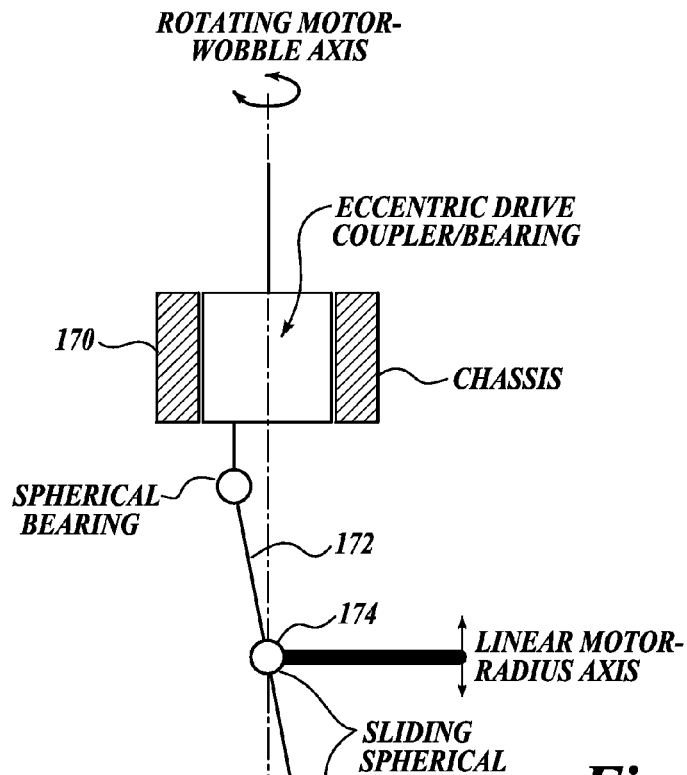
FIGS. 6A and 6B illustrate how the angular orientation of the focal zone is changed with the mechanism shown in FIG. 6.
Figure 6B:
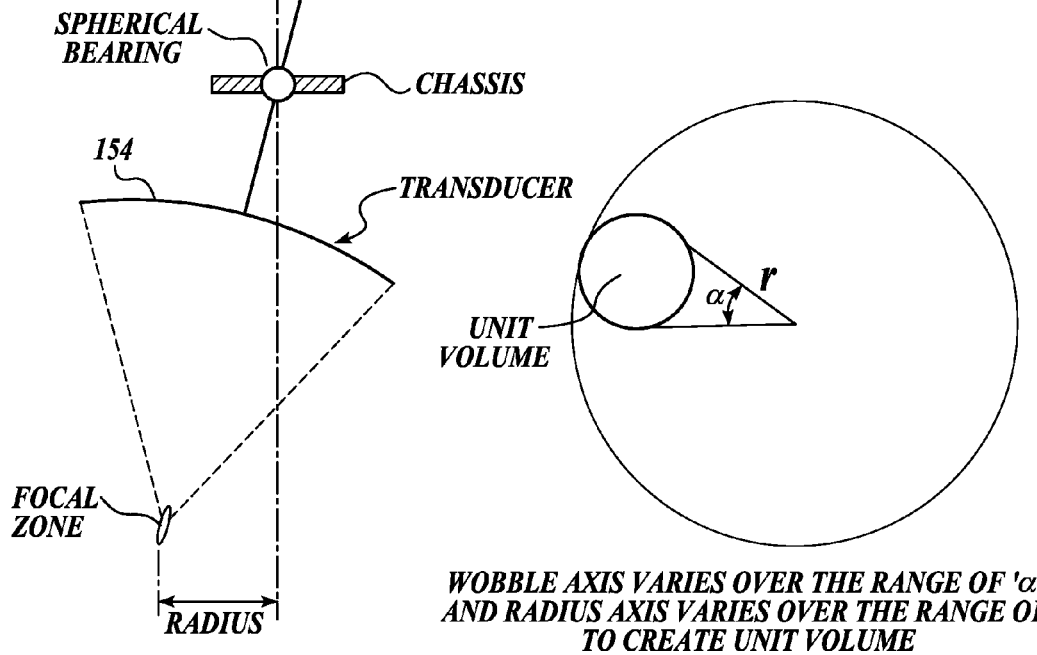

As shown in FIGS. 6A and 6B, by turning the shaft of the motor 168 and by changing the angular orientation of the focal zone of the HIFU transducer by adjusting the position of the spherical bearing 174 along the length of the shaft 172, toroidal rings of ablated tissue or annular patterns composed of ablated cylinders/spheres can be created in the body at various depths.

If the motors 164 and 168 are simultaneous rotated back and forth through a desired angle with signals that are approximately 90 degrees out of phase, the focal zone of the HIFU transducer will trace out a substantially circular pattern off a central axis of the treatment device 150, thereby allowing the creation of an elemental treatment volume at a desired location in the body as shown in FIG. 6B. By continuously rotating the motor 168 while the spherical bearing 174 is at the farthest point from the motor 168, the elemental treatment volume can be created at the top and bottom of the shell depending on the depth of the focal zone.

In one embodiment, to treat a desired tissue volume, a physician obtains an image of the tissue volume with the imaging transducer 152 and adjusts the radius of a marker ring on the image or interacts with some other graphical user interface or keyboard to define the boundaries of the desired shell. Based on the radius of the marker ring, a computer calculates the volume or shape of the ablated shell to be created in the body. The HIFU transducer and motors within the treatment device 150 are then activated such that a pattern of elemental treatment volumes is ablated to form the shell that surrounds or encapsulates the tissue volume or some other desired pattern of elemental treatment volumes. When creating elemental treatment volumes, the focal zone of the HIFU transducer may be continually moved until a treatment volume is ablated or the focal zone may be moved to discrete positions around the perimeter of the elemental treatment volumes and a HIFU signal applied to create the elemental treatment volumes.

In another embodiment, the linear actuator 160 that adjusts the focal zone depth, the linear actuator 164 that adjusts the angle of the HIFU transducer, and the motor 168 that rotates the shaft 172 are simultaneously operated to create a spiral shell ablation pattern of the type shown in FIG. 4C.

Following treatment, the patient may be injected with a contrast agent to allow the physician to confirm that blood perfusion has been appropriately reduced or eliminated within the targeted tissue volume. Non-perfusion would provide a strong indication that the treated tissue volume will undergo (or has undergone) ischemic necrosis. Such contrast agents are well known in the art for use with various different imaging modalities including ultrasound, MRI, x-ray, CT, etc.

Figure 6C:
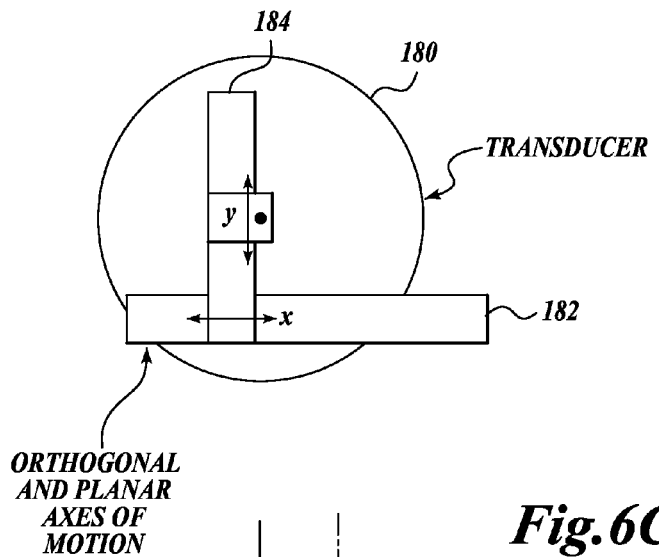
FIGS. 6C and 6D illustrate another mechanism for changing the depth and position of the focal zone.
Figure 6D:
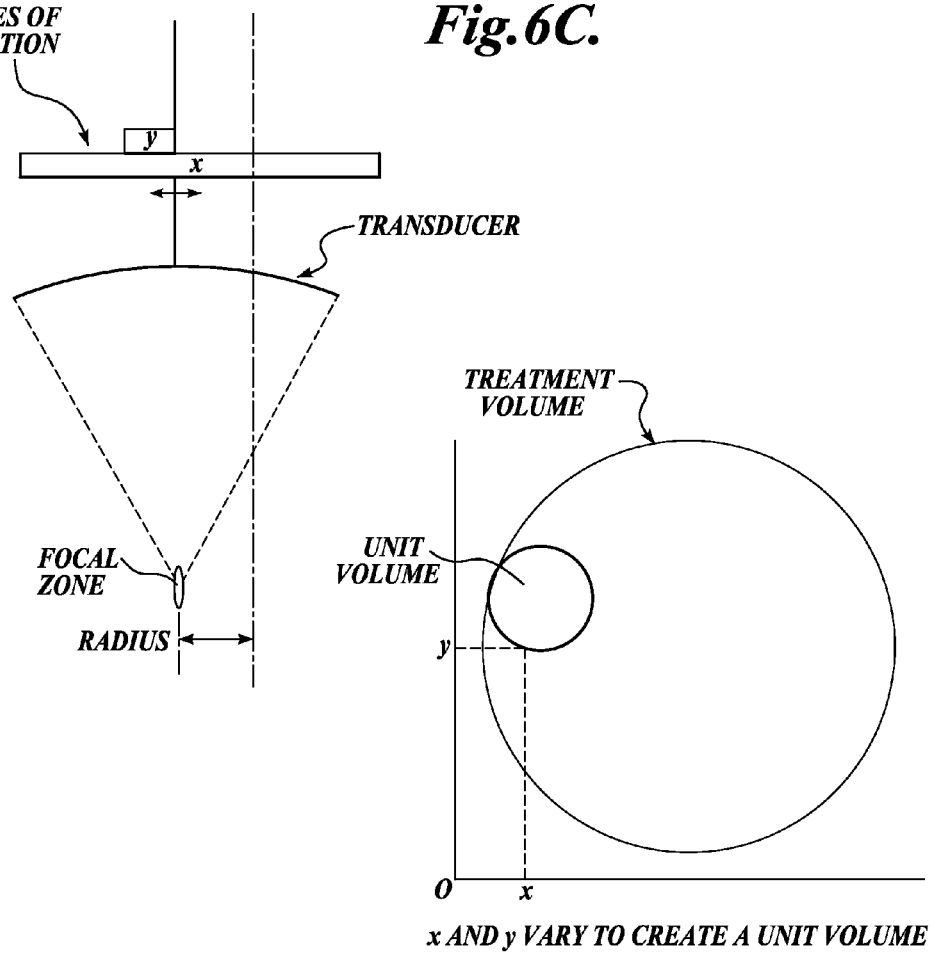

As will be appreciated, other mechanisms are possible to selectively position the focal zone of a HIFU transducer to create the elemental treatment volumes and treat the desired tissue volume. FIGS. 6C AND 6D illustrate another alternative embodiment where a transducer 180 is moved in two orthogonal directions (x,y) by a pair of linear actuators 182, 184. The linear actuators, which could be motors that drive a worm gear or other mechanisms, are computer controlled so that the position of the focal zone of the HIFU transducer 180 is moved as desired. A third motor or actuator (not shown) can be computer controlled to vary the height of the transducer 180 to change the depth of the focal zone.

Figure 7:
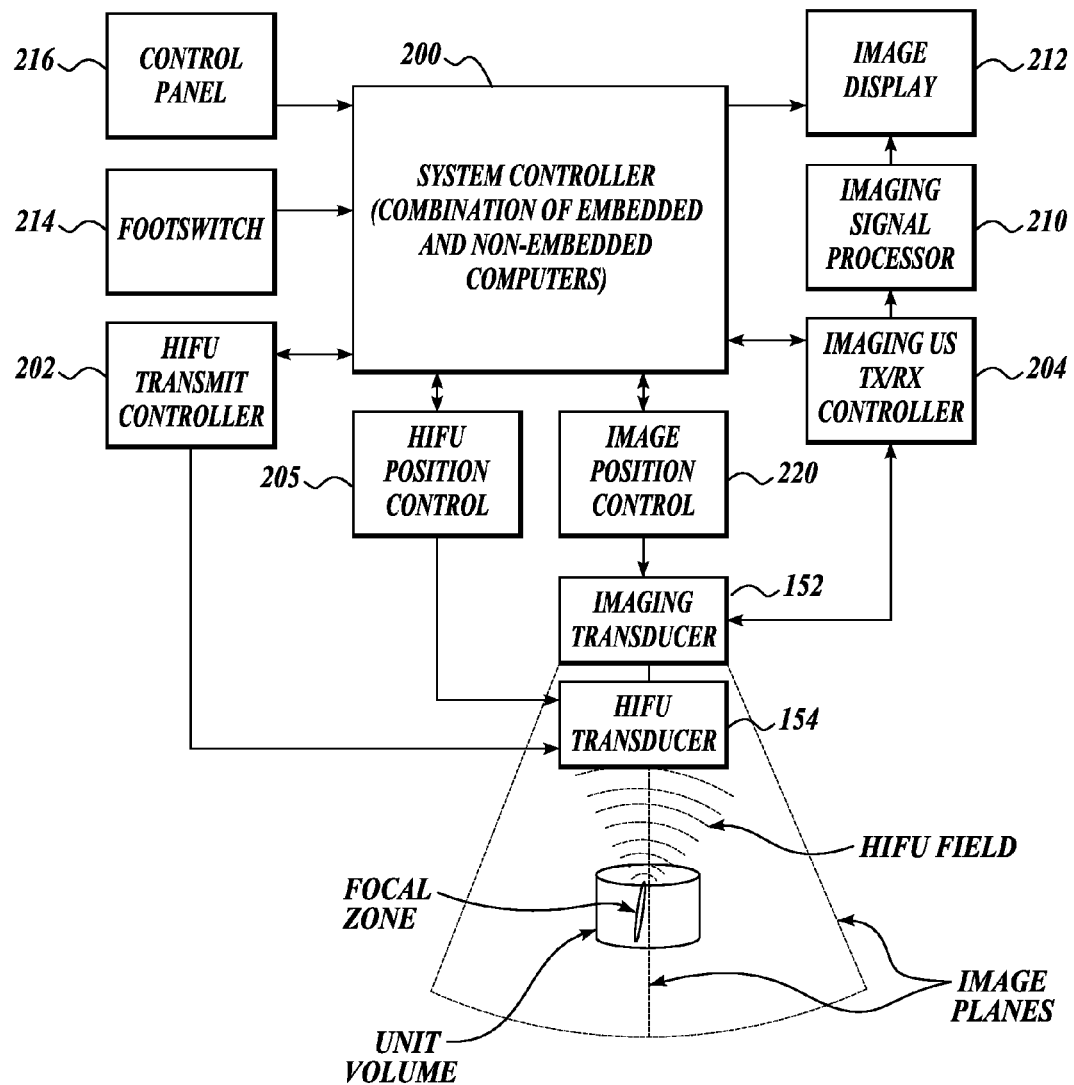
FIG. 7 illustrates a system for treating tissues with HIFU in accordance with an embodiment of the disclosed technology.

FIG. 7 illustrates a basic block diagram of a HIFU ultrasound treatment system in accordance with one embodiment of the disclosed technology. In this embodiment, a patient treatment device includes both a HIFU transducer 154 and an ultrasound imaging transducer 152. The transducers may be separate devices as shown in FIG. 6 or may be an integrated device with HIFU and imaging ultrasound elements located on the same transducer head. Controlling the operation of the imaging and HIFU transducers is a system controller 200 that may include one or more general purpose or special purpose programmed processors that are programmed to perform the functions described herein. The system controller 200 supplies control signals to a HIFU control unit 202 that selects the power of the HIFU signals to be provided by the HIFU transducer 154.

In one embodiment, the operating power level is selected by transmitting a number of test signals at different power levels and analyzing the echo signals created in response to the transmitted test signals. The operating power level for HIFU treatment is selected when a desired characteristic of an echo signal, such as a ratio of the power of different frequency components within the echo signal, begins to saturate. In one embodiment, the operating power selected is that which causes the power of the second harmonic signal to saturate irrespective of further increases in the power of the fundamental frequency of the HIFU signal. Further detail of possible methods of selecting and controlling the HIFU power can be found in U.S. patent application Ser. No. 12/537,217 filed Aug. 6, 2009 and which is herein incorporated by reference.

The imaging transducer 152 is controlled by an imaging ultrasound controller 204 that includes conventional ultrasound components such as a transmit/receive switch, beam former, RF amplifiers and signal processors. The output of the ultrasound controller 204 is fed to an ultrasound signal processor 210 that operates to produce ultrasound imaging signals for display on a video monitor 212 or other display. The image signals can also be stored on a computer readable media (DVD etc, video tape), printed by a printer or otherwise stored for later diagnosis or analysis.

A computer controlled steerer 205 is controlled by the system controller 200 to create a number of elemental treatment volumes to treat a desired volume of tissue. In one embodiment, the computer controlled steerer 205 mechanically adjusts the angular orientation or x,y position of the HIFU transducer 154 and the depth of the focal zone to direct the HIFU energy at a desired location. In another embodiment, the computer controlled steerer 205 electronically adjusts the angular orientation or x,y position of the focal zone of the HIFU transducer 154 and the depth of the focal zone of the HIFU transducer 154 to create the elemental treatment volumes.

A footswitch 214 allows a physician or their assistant to selectively deliver HIFU energy to the patient in order to treat a tissue site. In addition, the physician can manually change the size and shape of the treatment volume and other functions of the system using one or more controls on a control panel 216.

In some embodiments, the system may include an image position control 220 that changes the orientation of the imaging transducer 152 so that the physician can view the desired target tissue volume to be treated at different angles or in different planes. The image position control be either mechanical or electronic and is controlled by the system controller 200.

While illustrative embodiments have been illustrated and described, it will be appreciated that various changes can be made therein without departing from the scope of the invention. For example, although the energy source used to create the ablated shell is HIFU in the disclosed embodiments, other energy sources could be used such as radiation, lasers, rf, microwaves, cryoablation, etc. Some of these energy sources are minimally invasive such that they must be delivered to the tissue volume with a catheter, endoscope, or the like. Applying energy from these energy sources ablates the perimeter of the tissue volume to create an ablated shell. In another embodiment, the HIFU transducer may be insertable in to the body such as transvaginally or rectally. If the tissue volumes to be treated can be seen from the location of the HIFU transducer, then images of the tissue can be obtained with image sensors other than ultrasound image sensors. In some embodiments, the imaging of the desired treatment volume may be done with another type of imaging modality such as MRI, x-ray, infrared, or the like in a manner that allows a physician to confirm that the HIFU is being delivered to the area of desired target tissue volume. Therefore, the scope of the invention is to be determined from the following claims and equivalents thereof.

The embodiments of the invention in which an exclusive property or privilege is claimed are defined as follows:

1. A system for treating a desired treatment volume of tissue with high intensity focused ultrasound (HIFU), comprising:
a HIFU applicator;
a HIFU transducer operating within the HIFU applicator, wherein the HIFU transducer is configured to deliver treatment energy to a focal zone; and
a processor programmed to repeatedly move the focal zone in an enclosed trajectory over or along a perimeter of an elemental treatment volume of tissue,
wherein the processor is programmed to position the focal zone in a pattern that creates a plurality of elemental treatment volumes distributed laterally and vertically at a periphery of the desired treatment volume such that an interior region of the desired treatment volume is indirectly treated by heating from the elemental treatment volumes but the interior region of the desired treatment volume is outside the enclosed trajectories of the elemental treatment volumes, and
wherein, for each elemental treatment volume, the focal zone moves over or along the same trajectory more than once as treatment energy is delivered in multiple doses to the tissue in the trajectory.

2. The system of claim 1, wherein the processor is programmed to control movement of the focal zone to indirectly treat an interior region of each elemental treatment volume by indirect heating as the treatment energy is delivered to the perimeter of the elemental treatment volume.

3. The system of claim 1, wherein the processor is programmed to repeatedly position the HIFU transducer in a pattern that creates a number of elemental treatment volumes within the desired treatment volume.

4. The system of claim 1, wherein the plurality of elemental treatment volumes creates a shell at the periphery of the desired treatment volume.

5. The system of claim 1, wherein the treatment energy is non-linear at the focal zone.

6. The system of claim 1, wherein at least one elemental treatment volume is cylindrical and has a diameter approximately equal to a length of the focal zone.

7. The system of claim 1, wherein the processor is programmed to control a vertical position of the HIFU transducer relative to the desired treatment volume.

8. The system of claim 1, wherein the processor is programmed to control an electronic beam steerer.

9. The system of claim 1, wherein the processor is further programmed to control the delivery of treatment energy such that the tissue of each elemental treatment volume is at least partially ablated with each pass of the focal zone over or along the perimeter of the elemental treatment volume.

10. The system of claim 1, wherein the HIFU applicator remains stationary while the focal zone of the HIFU transducer is moved in the trajectory over or along the perimeter of the elemental treatment volume.

11. A system for treating a desired treatment volume of tissue with high intensity focused ultrasound (HIFU), comprising:
a HIFU applicator;
a HIFU transducer associated with the HIFU applicator, wherein the HIFU transducer is configured to deliver treatment energy to a focal zone; and
means for positioning the focal zone to create a plurality of elemental treatment volumes at a periphery of the desired treatment volume of tissue by repeatedly positioning the focal zone in an enclosed trajectory over or around a perimeter of each elemental treatment volume,
wherein the focal zone moves over or along the same trajectory more than once as multiple doses of the treatment energy are delivered to tissue in the trajectory, wherein an outer region of each elemental treatment volume is directly treated by the treatment energy and an interior region of the elemental treatment volume is indirectly treated, and wherein an interior region of the desired treatment volume is indirectly treated from treatment energy delivered to the elemental treatment volumes but the interior region of the desired treatment volume is outside the enclosed trajectories of the elemental treatment volumes.

12. The system of claim 11, wherein at least one elemental treatment volume is cylinder-shaped and has a diameter substantially equal to a length of the focal zone.

13. The system of claim 11, wherein at least one elemental treatment volume is cylinder-shaped and has a diameter that is larger than twice the diameter of the focal zone.

14. The system of claim 13, wherein the at least one elemental treatment volume has a height substantially equal to the length of the focal zone.

15. The system of claim 11, wherein the means for positioning the focal zone includes a mechanical linkage configured to rotationally position the HIFU transducer around a central axis such that the focal zone repeatedly moves in the closed trajectory around the perimeter of each elemental treatment volume.

16. The system of claim 11, wherein the means for positioning the focal zone includes an electronic beam steerer configured to electronically orient the focal zone of the HIFU transducer such that the focal zone is repeatedly positioned in the closed trajectory around the perimeter of the elemental treatment volume.

17. The system of claim 11, wherein the means for positioning the focal zone further creates a pattern of elemental treatment volumes within the desired treatment volume of tissue.

18. The system of claim 11, wherein the elemental treatment volumes are laterally and vertically distributed at the periphery of the desired treatment volume of tissue and define a shell that encompasses at least a portion of the desired treatment volume of tissue.

19. The system of claim 11, wherein the treatment energy is a HIFU signal that is non-linear in tissue at the focal zone.

20. The system of claim 11, wherein the HIFU applicator remains stationary while the means for positioning the focal zone repeatedly positions the focal zone in the enclosed trajectory over or around the perimeter of each elemental treatment volume.

21. A method of operating a high intensity focused ultrasound (HIFU) device to treat a desired treatment volume of tissue, comprising:

selectively controlling the position of a focal zone of a HIFU transducer that is operating within a HIFU applicator, wherein the HIFU transducer is configured to apply treatment energy at the focal zone in a path around a perimeter of an elemental treatment volume of tissue;

applying treatment energy to the tissue while the focal zone is oriented at a number of positions around the perimeter of the elemental treatment volume, wherein the focal zone is positioned in the same path more than once as treatment energy is applied to tissue in the path, and wherein tissue at the perimeter of the elemental treatment volume is ablated by repeated direct exposure to the treatment energy and tissue at an interior of the elemental treatment volume is indirectly treated by heat from the tissue at the perimeter of the elemental treatment volume; and positioning the focal zone in a pattern that creates a plurality of elemental treatment volumes at a periphery of the desired treatment volume of tissue such that an interior region of the desired treatment volume of tissue is outside the perimeters of the elemental treatment volumes but is indirectly treated by heat from the treatment energy applied to the perimeters of the elemental treatment volumes.

22. The method of claim 21, further comprising selectively controlling the position of the focal zone to create a pattern of elemental treatment volumes within the desired treatment volume of tissue.

23. The method of claim 21, wherein the pattern defines a shell of laterally and vertically distributed elemental treatment volumes that partially or completely encapsulates the desired treatment volume of tissue.

24. The method of claim 23, wherein the position of the focal zone is controlled to create a pattern of elemental treatment volumes that are sufficiently close together to form the shell.

25. The method of claim 23, further comprising selectively controlling the position of the focal zone to create two or more shells within the desired treatment volume of tissue.

26. The method of claim 21, wherein the focal zone is selectively positioned such that treatment energy is applied over a diameter that is approximately equal to a length of the focal zone to create the elemental treatment volume.

27. The method of claim 21, wherein applying the treatment energy includes delivering HIFU signals that are non-linear at the focal zone to the tissue.

28. The method of claim 21, further comprising:
displaying an image of the tissue on a display screen;
receiving input that indicates a boundary of the desired treatment volume of tissue; and
determining the pattern for moving the focal zone to create the plurality of elemental treatment volumes sufficiently adjacent to one another to form an ablated shell that encapsulates some or all of the desired treatment volume of tissue, based on the received input.

29. The method of claim 21, wherein the focal zone of the HIFU transducer is repeatedly positioned around the perimeter of each elemental treatment volume and treatment energy is applied in multiple doses such that the tissue of each elemental treatment volume is at least partially ablated with each pass of the focal zone around the perimeter of the elemental treatment volume.

30. The method of claim 21, wherein the treatment energy is a pulsed HIFU signal.

31. The method of claim 21, further comprising holding the HIFU applicator stationary while repeatedly positioning the focal zone in the path around the perimeter of the elemental treatment volume.

* * * * *